United States Patent
Bertolero et al.

(10) Patent No.: US 6,309,349 B1
(45) Date of Patent: Oct. 30, 2001

(54) SURGICAL RETRACTOR AND STABILIZING DEVICE AND METHOD FOR USE

(75) Inventors: Arthur A. Bertolero; Raymond S. Bertolero, both of Danville; Jerome B. Riebman, Sunnyvale, all of CA (US)

(73) Assignee: Endoscopic Technologies, Inc., Danville, CA (US)

( * ) Notice: Subject to any disclaimer, the term of this patent is extended or adjusted under 35 U.S.C. 154(b) by 0 days.

(21) Appl. No.: 09/171,207

(22) PCT Filed: Apr. 10, 1997

(86) PCT No.: PCT/US97/05910
§ 371 Date: Jul. 6, 1999
§ 102(e) Date: Jul. 6, 1999

(87) PCT Pub. No.: WO97/37596
PCT Pub. Date: Oct. 16, 1997

Related U.S. Application Data

(60) Provisional application No. 60/014,922, filed on Apr. 10, 1996.

(51) Int. Cl.[7] .................................................. A61B 1/32
(52) U.S. Cl. .................... 600/213; 600/219; 600/210; 600/215; 600/235
(58) Field of Search .................... 600/201, 206, 600/210, 213, 219, 227, 231, 232, 215, 222, 235

(56) References Cited

U.S. PATENT DOCUMENTS

| | | | |
|---|---|---|---|
| 861,356 | * 7/1907 | Buchfeld | 600/219 |
| 1,655,962 | 1/1928 | Lespinasse . | |

(List continued on next page.)

FOREIGN PATENT DOCUMENTS

| | | |
|---|---|---|
| 669511 | 8/1963 | (CA) . |
| WO 97/37581 | 10/1997 | (WO) . |
| WO 97/37597 | 10/1997 | (WO) . |
| WO 97/37716 | 10/1997 | (WO) . |

OTHER PUBLICATIONS

Brochure for Snowden Pencer EndoCABG System, "Innovative Instrument for Endoscopic Coronary Artery Bypass Grafting," 3 pages (no date).

(List continued on next page.)

Primary Examiner—Jeffrey A. Smith
(74) Attorney, Agent, or Firm—Cooley Godward LLP

(57) ABSTRACT

An adjustable surgical retractor and its use for improving a surgeon's ability to perform closed-chest video-assisted exploratory, diagnostic or surgical procedures on a patient. The surgical retractor is designed to have opposable blades which can be inserted into a surgical incision in a patient undergoing a surgical procedure then spread apart to form an elongated access opening through which a instrument may be inserted to perform exploratory, diagnostic or surgical procedures. The blades used in the surgical retractor may be flexible or rigid and are attachable to the retractor. The blades are of a width, depth and thickness to provide an access to an internal cavity or subcutaneous region to allow greater degrees of freedom to the surgeon in inserting instruments into the access opening. The use of the surgical retractor forms a substantially ovoid channel, through which a medical instrument can be inserted to aid a doctor in performing surgical or other operations.

26 Claims, 18 Drawing Sheets

U.S. PATENT DOCUMENTS

| | | |
|---|---|---|
| 2,075,534 | 3/1937 | McCormack . |
| 2,977,958 * | 4/1961 | Seiger ............................... 600/277 X |
| 3,035,582 * | 5/1962 | Seiger ............................... 600/227 X |
| 3,038,467 | 6/1962 | Sovatkin . |
| 3,766,910 | 10/1973 | Lake . |
| 3,893,454 | 7/1975 | Hagelin . |
| 3,965,890 * | 6/1976 | Gauthier . |
| 4,754,746 | 7/1988 | Cox . |
| 4,813,401 | 3/1989 | Grieshaber . |
| 4,896,661 * | 1/1990 | Bogert et al. .................... 600/219 X |
| 5,297,538 | 3/1994 | Daniel . |
| 5,299,563 * | 4/1994 | Seton . |
| 5,584,803 | 12/1996 | Stevens et al. . |
| 5,613,937 | 3/1997 | Garrison et al. . |
| 5,618,260 | 4/1997 | Caspar et al. . |
| 5,752,526 * | 5/1998 | Cosgrove ............................. 128/898 |

OTHER PUBLICATIONS

Brochure for USSC Mini–CABG Instruments, "For Minimally Invasive Cardiac Surgery," 3 pages (1997).

Online Brochure for CTS MIDCAB System, "CTS Procducts: Selective Revascularization—MIDCAB Products," http://www.cardioth.com/physician/html/products/midcab.html, 2 pages (no date).

Online Brochure for Snowden Pencer Retractor, "Plastic Surgery Instruments," http://www.snowdenpencer.com/, 3 pages (no date).

Kirkland et al., *Cardiac Surgery*, vol. 1, Chap. 2, $2^{nd}$ Ed., pp. 101 (no date).

* cited by examiner

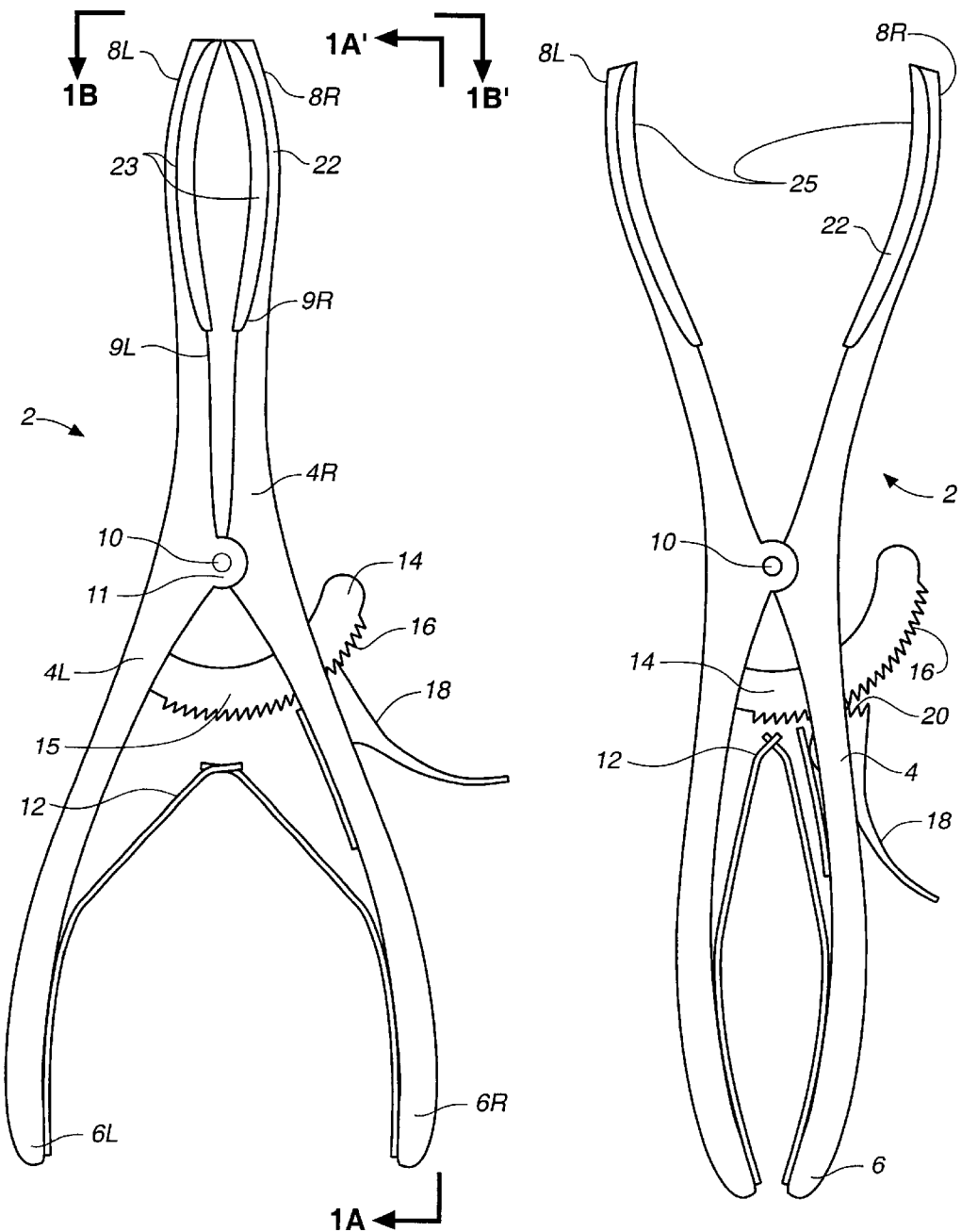

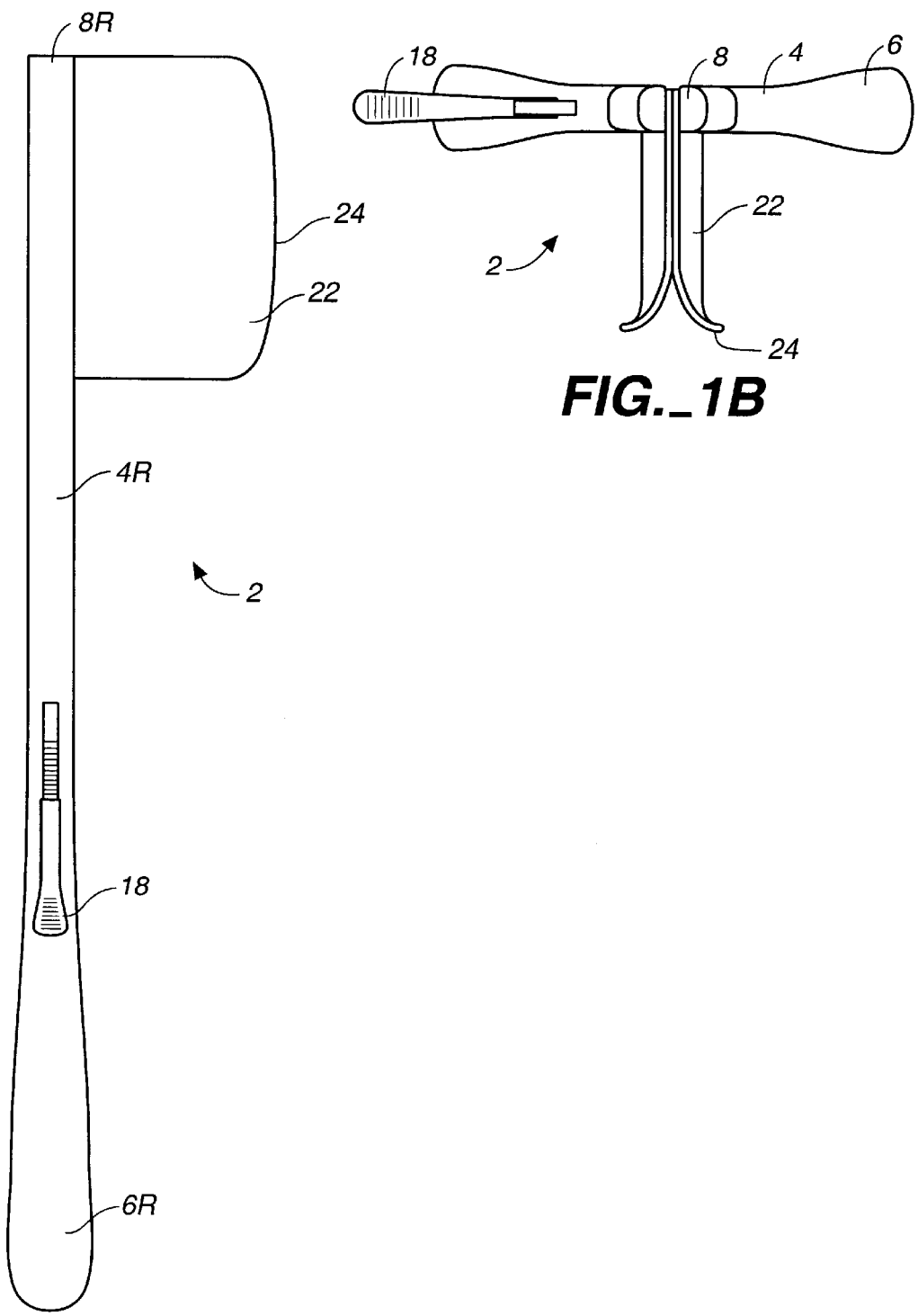
FIG._1B
FIG._1A

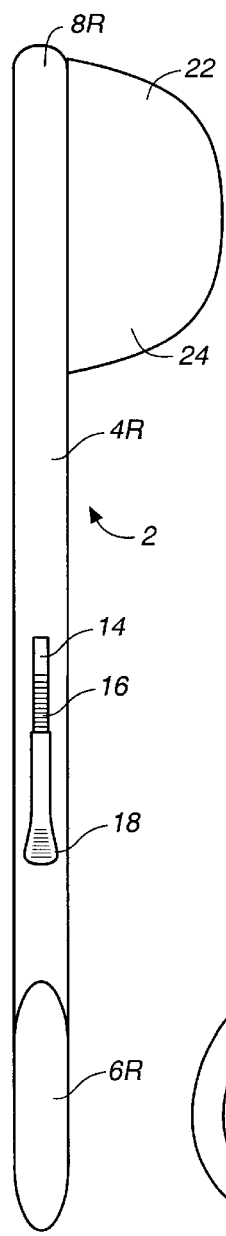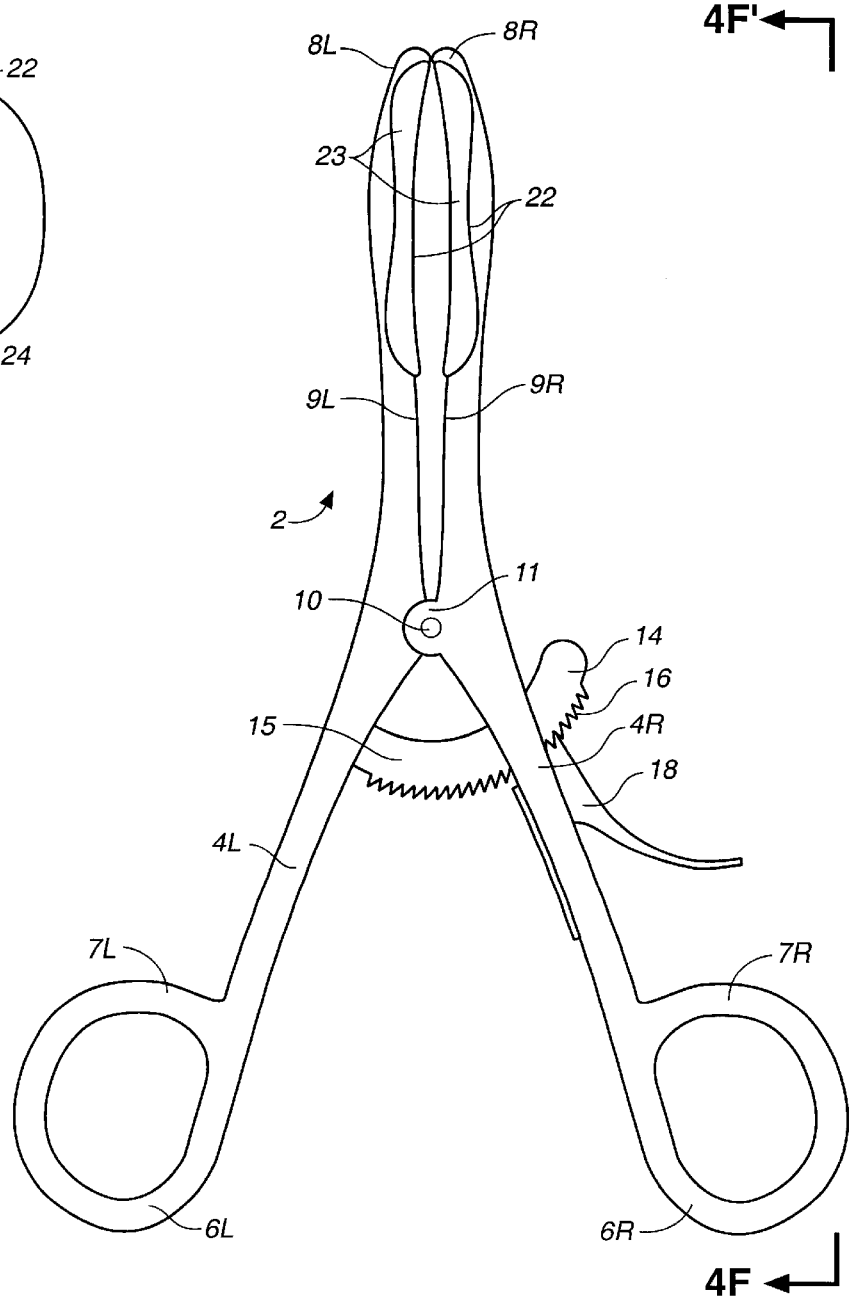
FIG._4   FIG._3

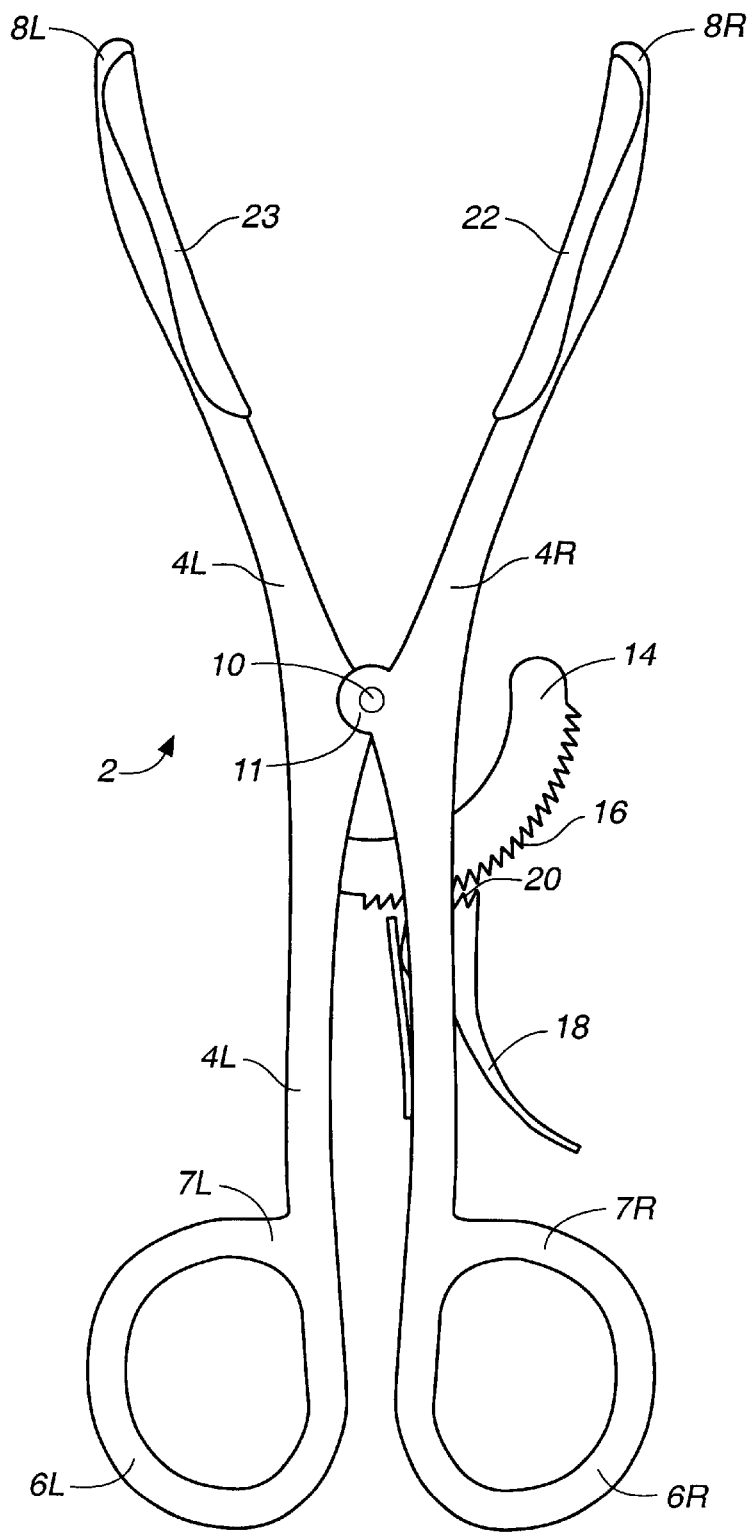
FIG._3A

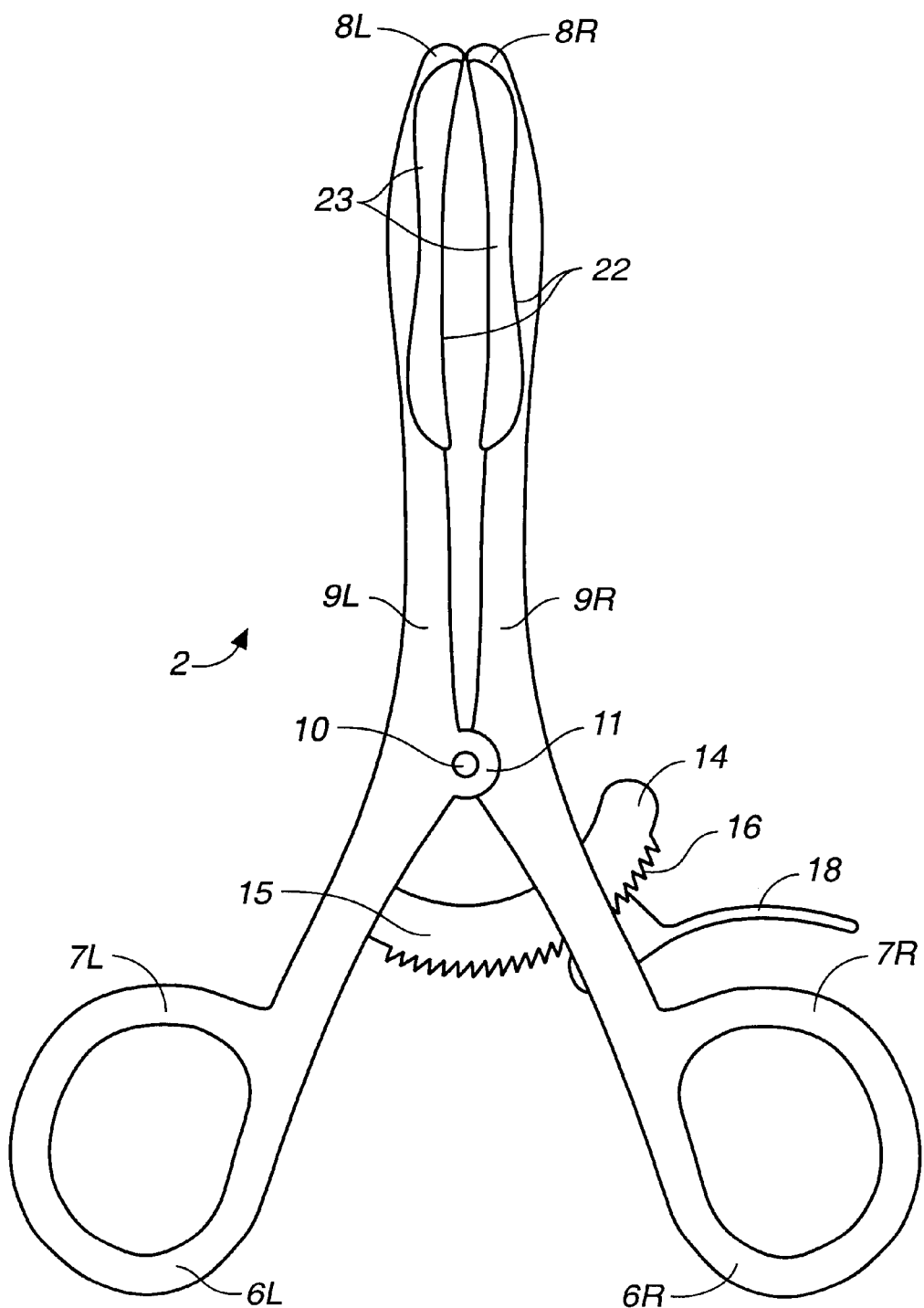
FIG._5

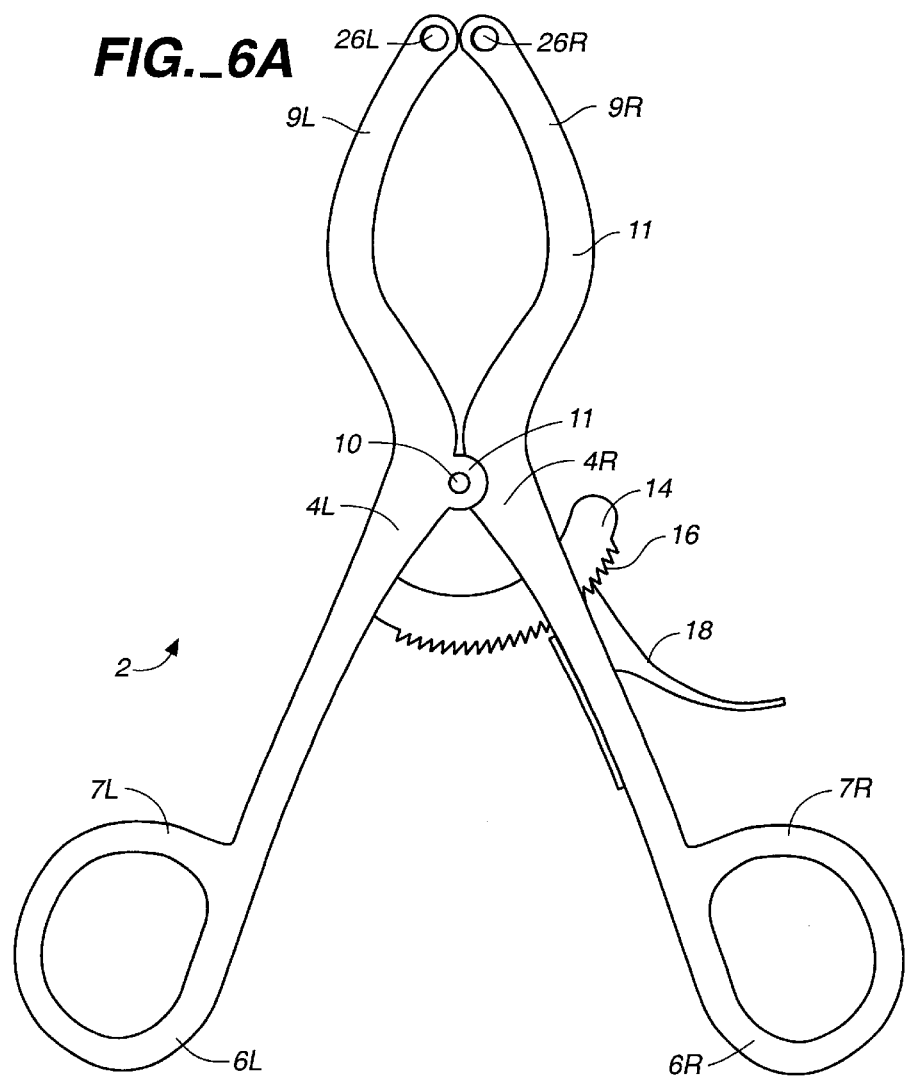
FIG._6A
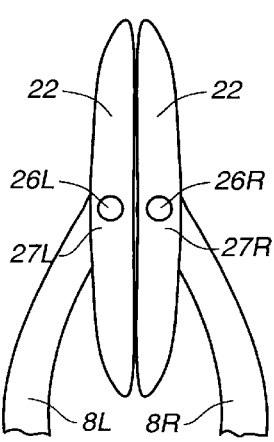
FIG._6E
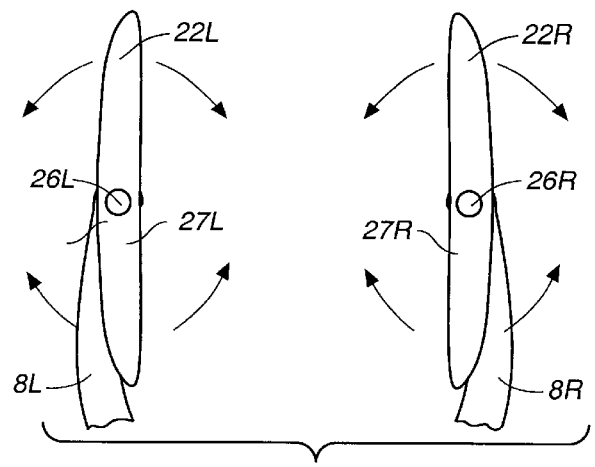
FIG._6F

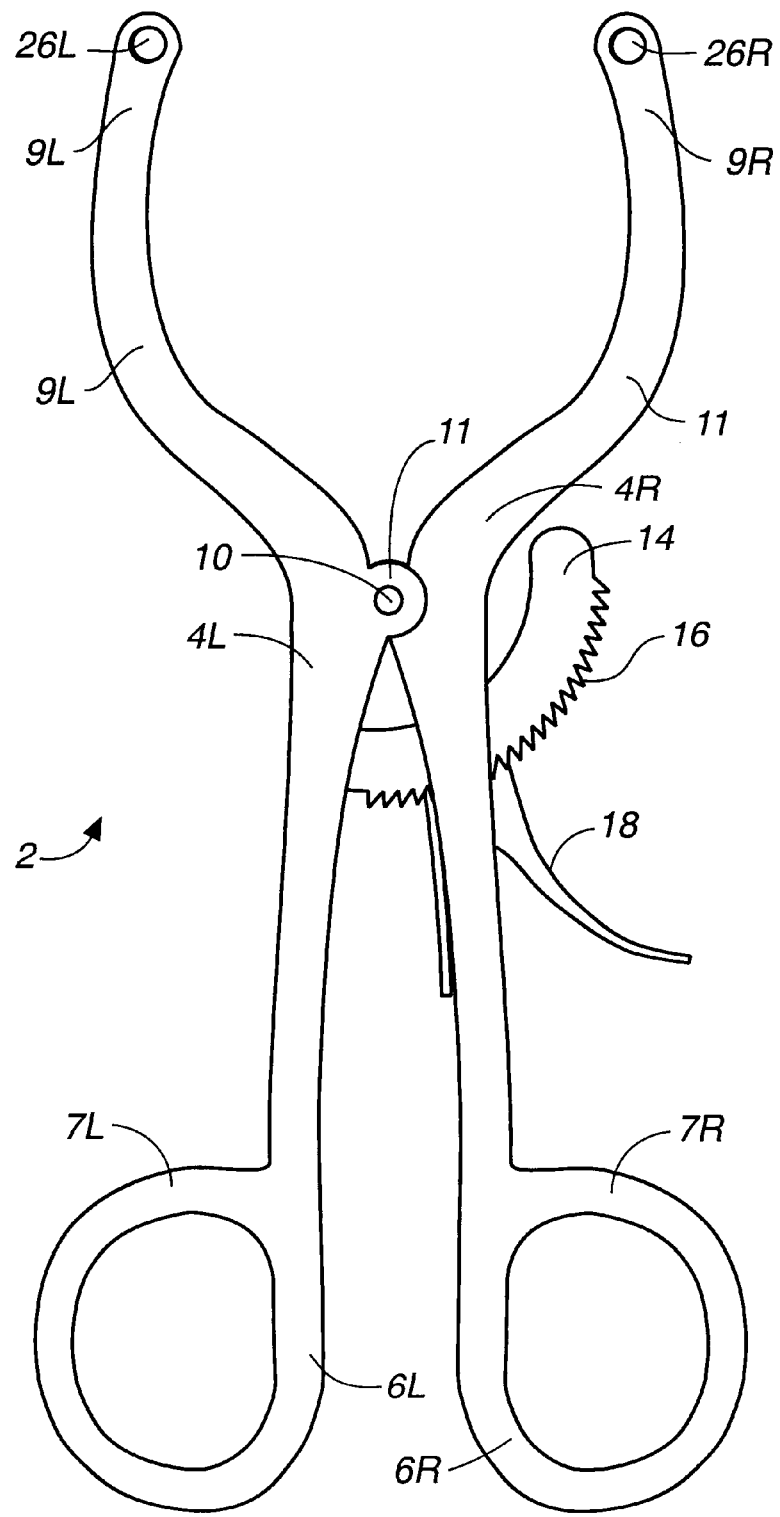
FIG._6B

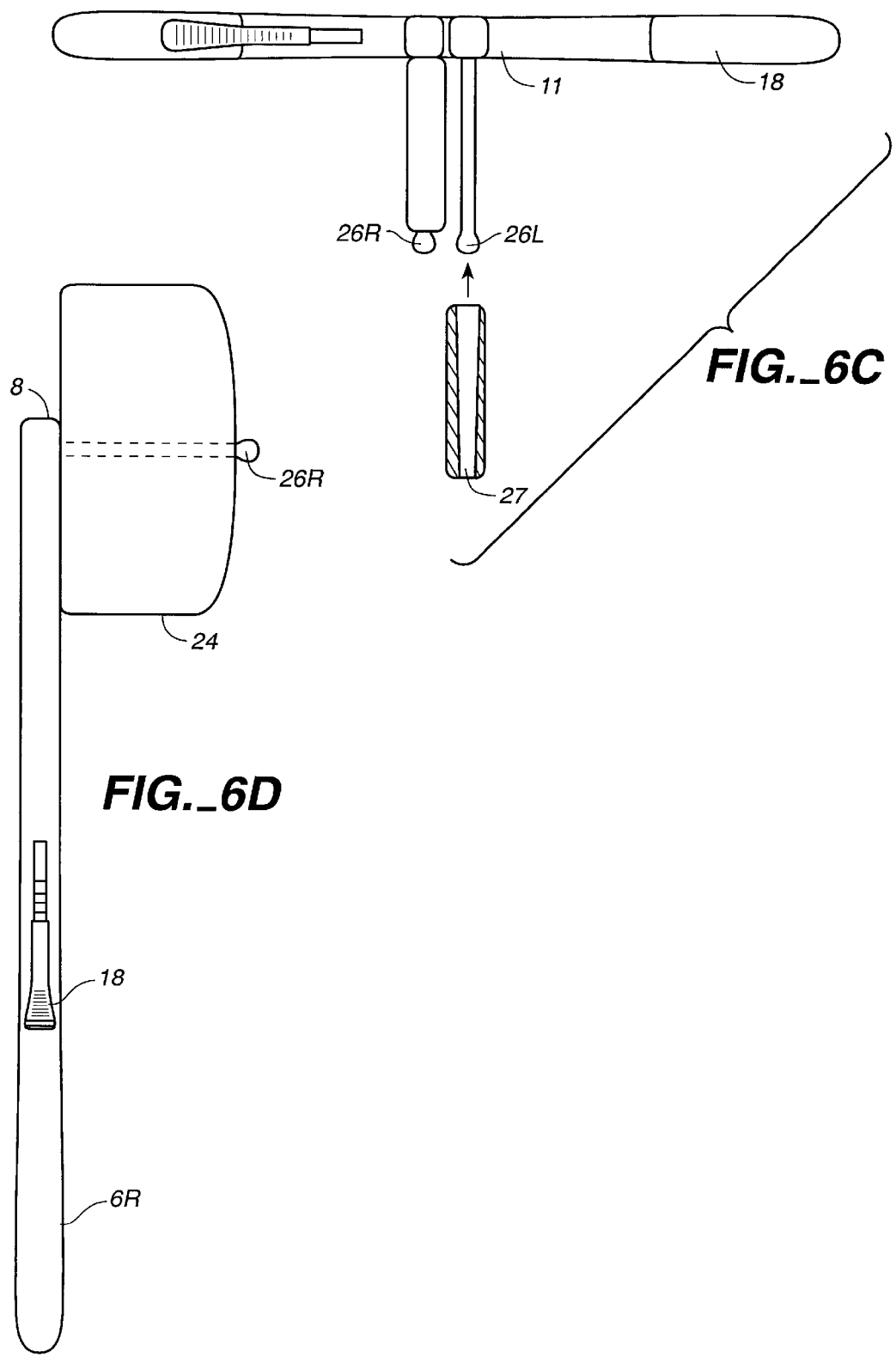

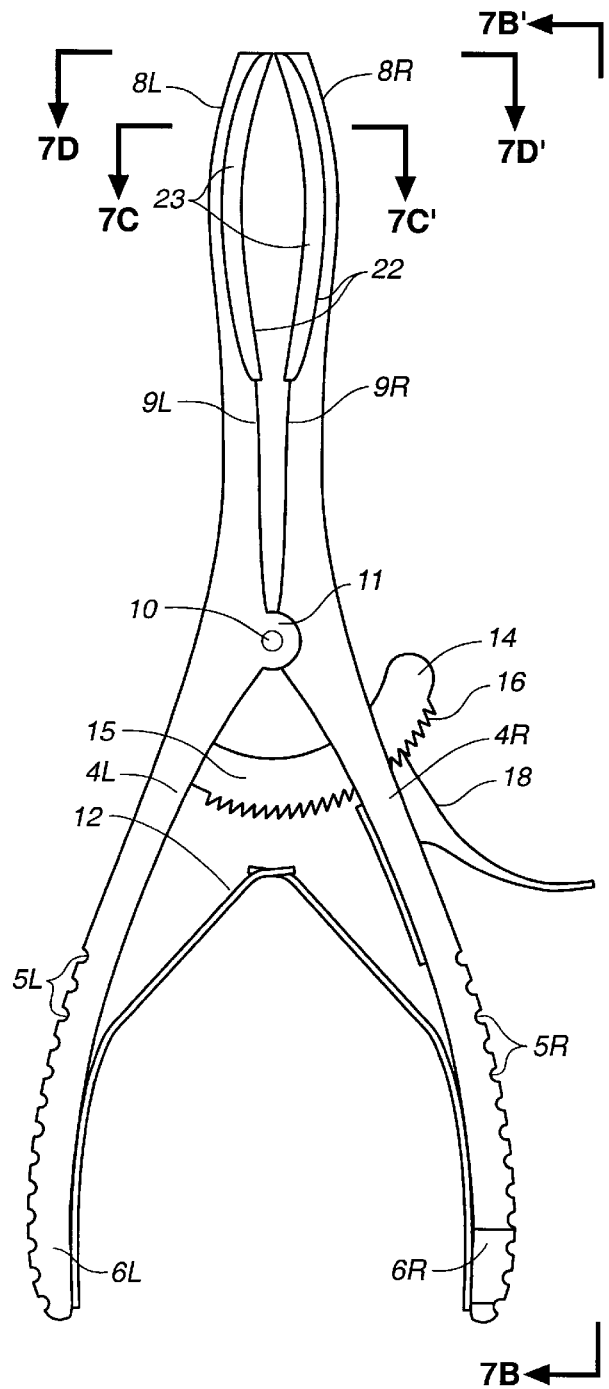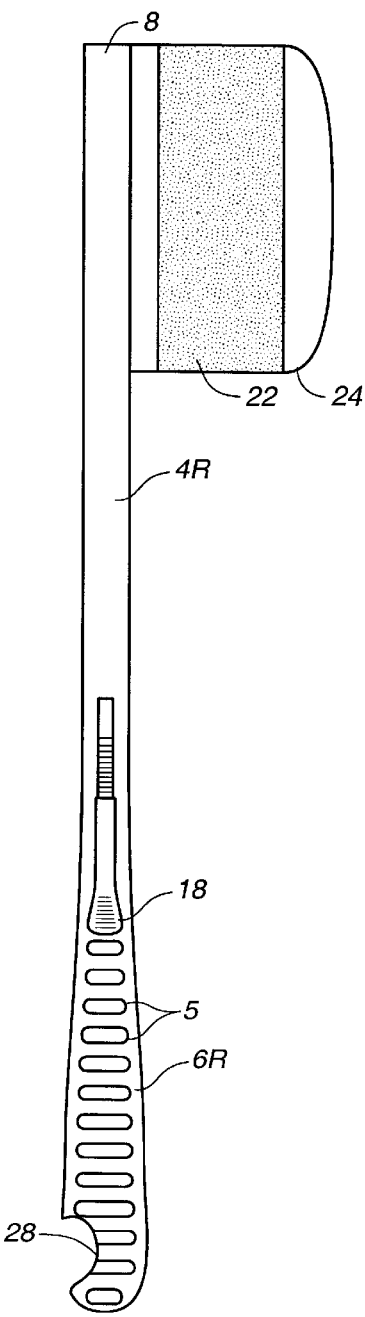
*FIG._7A*  *FIG._7B*

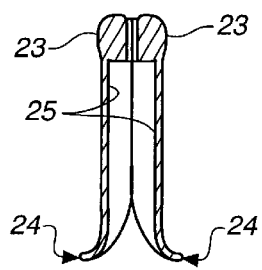
FIG._7C
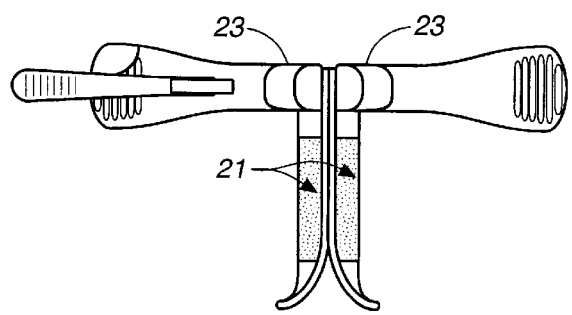
FIG._7D
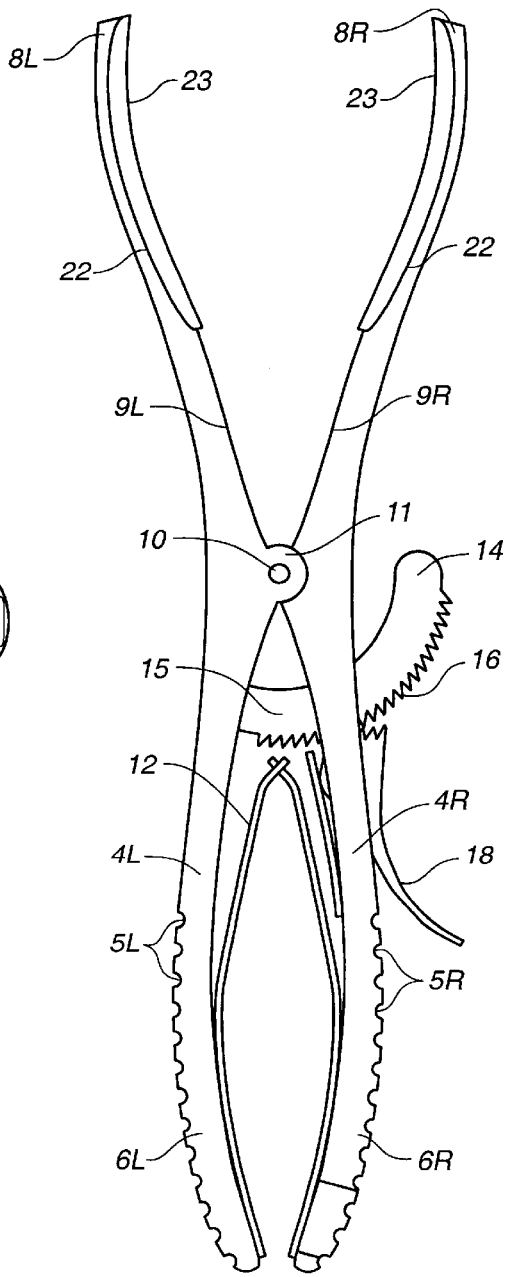
FIG._7E

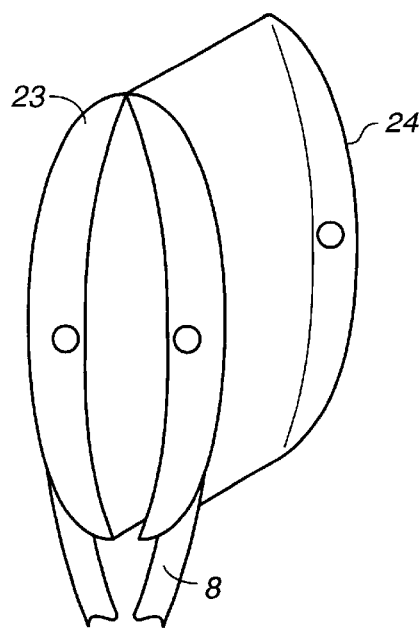
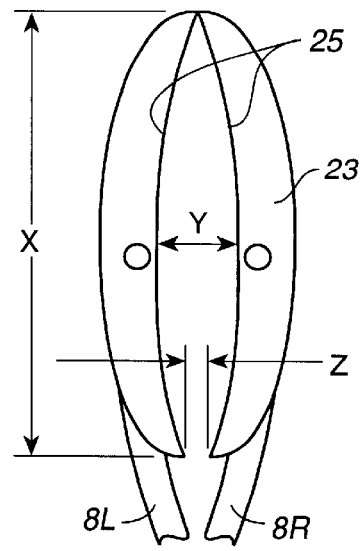
FIG._8A  FIG._8B
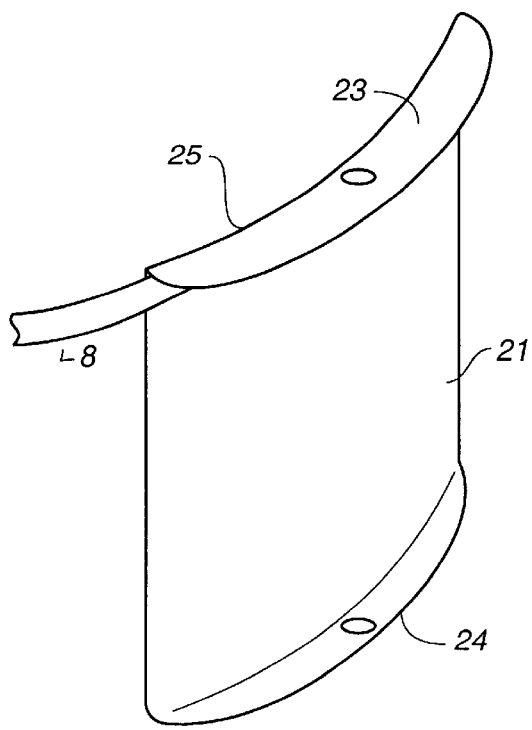
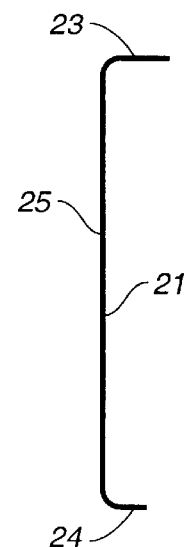
FIG._10A  FIG._10B

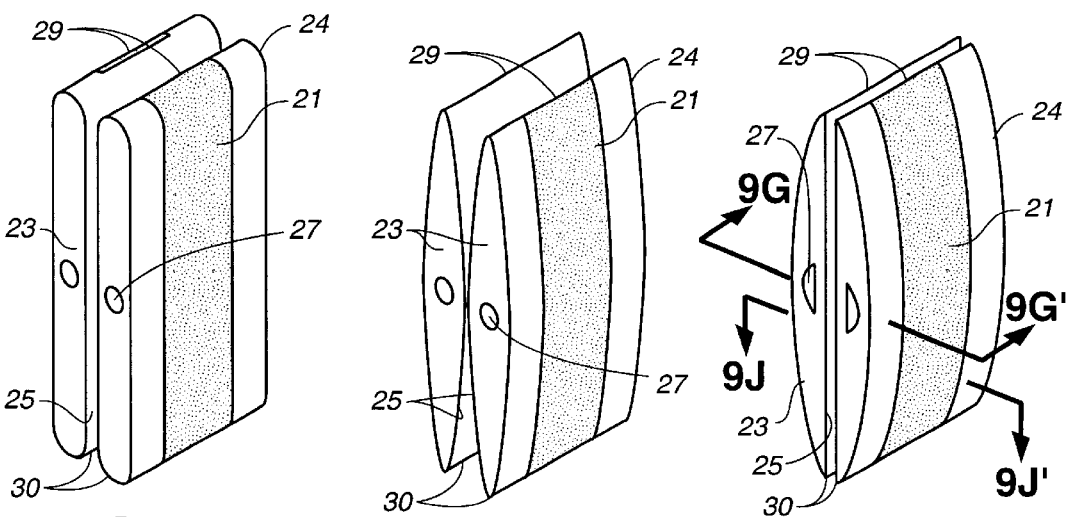
FIG._9A FIG._9B FIG._9C
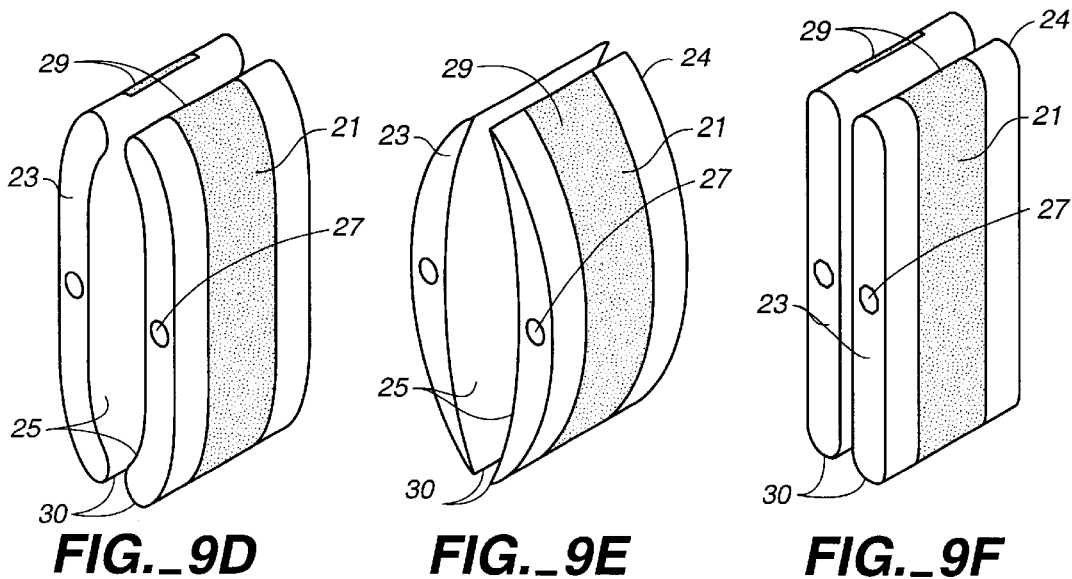
FIG._9D FIG._9E FIG._9F
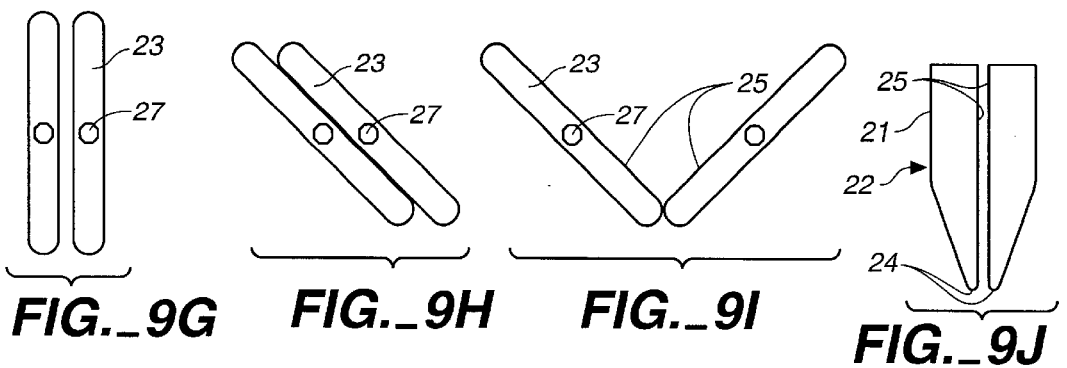
FIG._9G FIG._9H FIG._9I FIG._9J

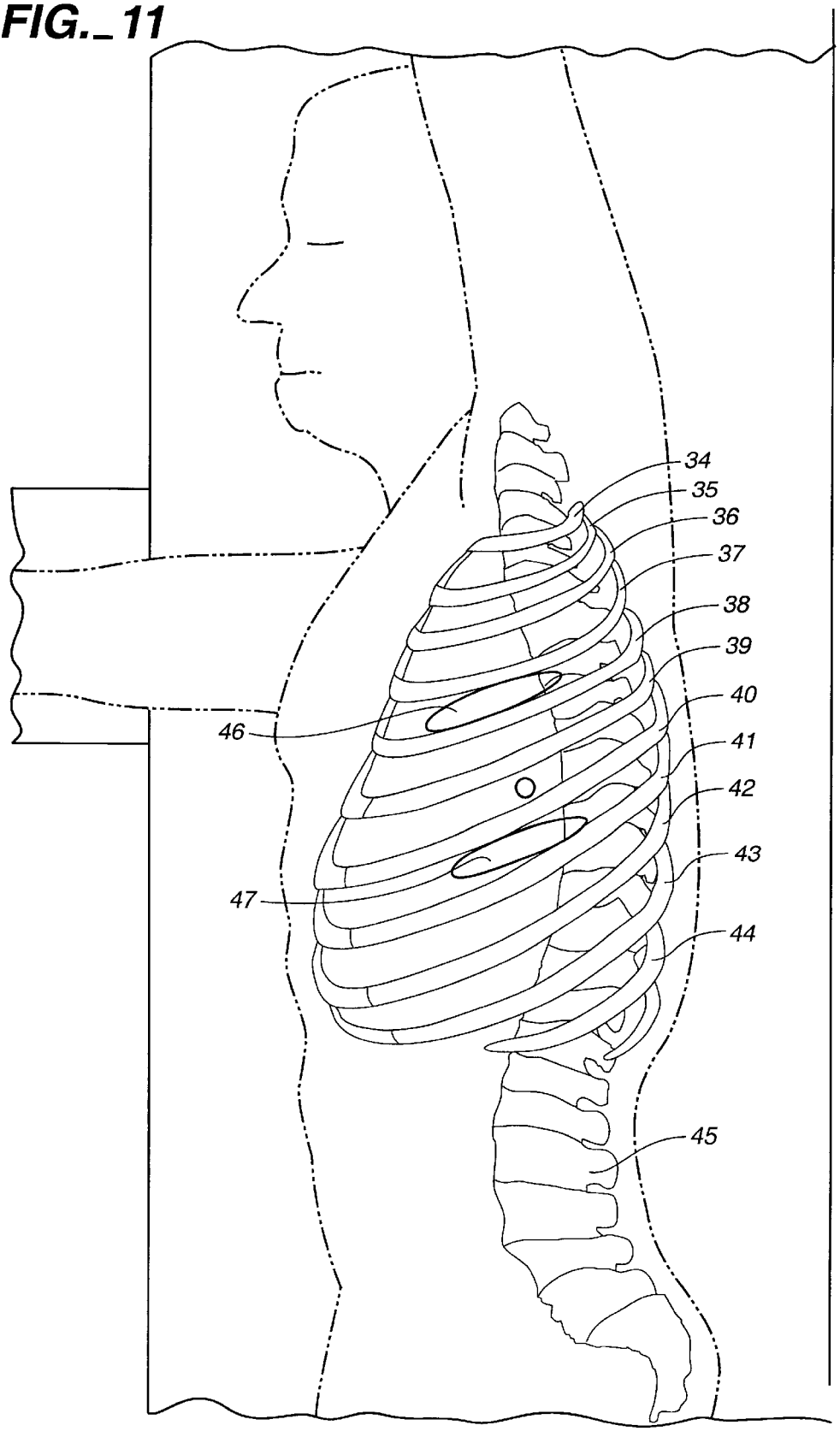
FIG._11

FIG._12A
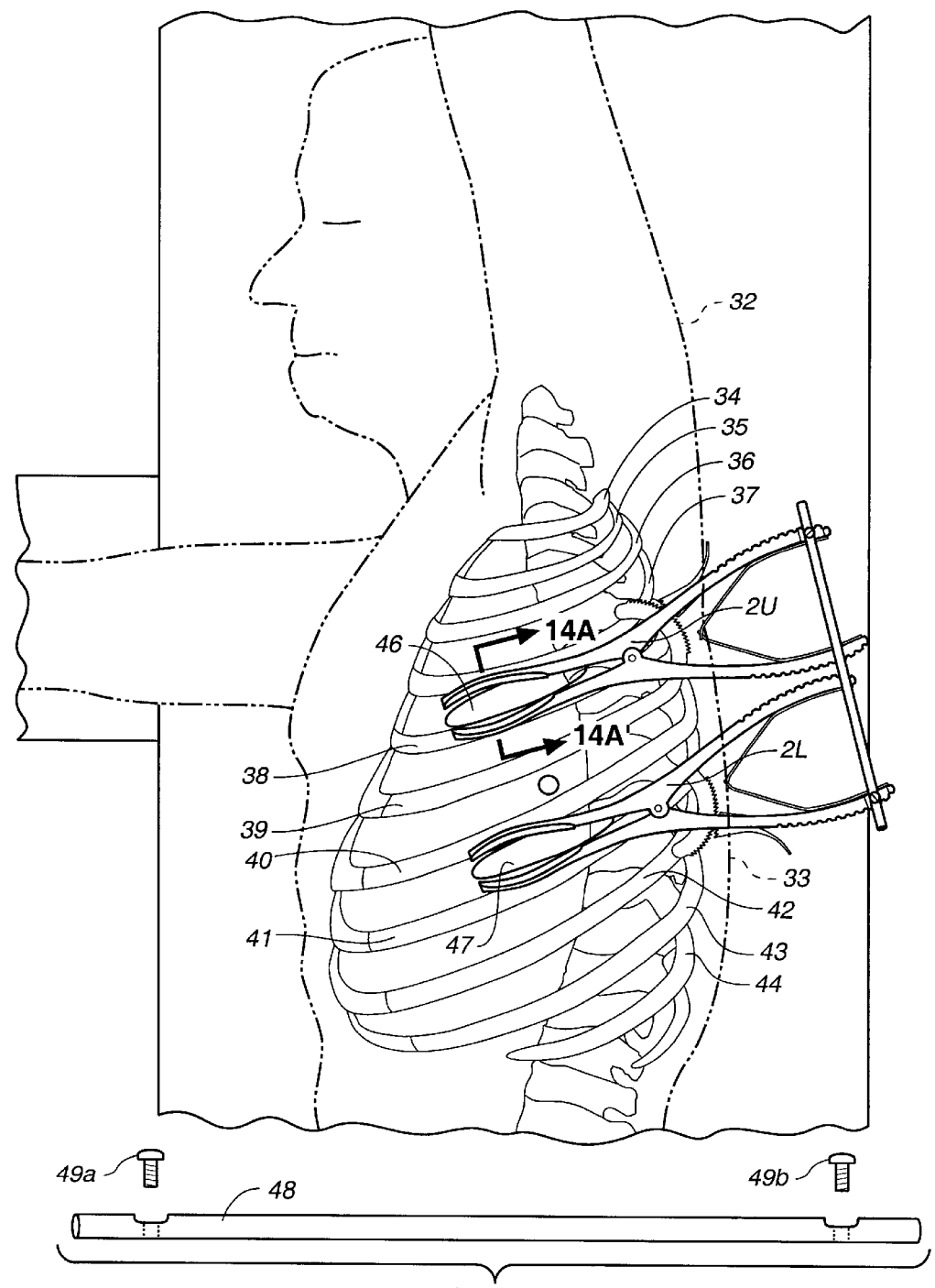
FIG._12B
FIG._12C

FIG._13
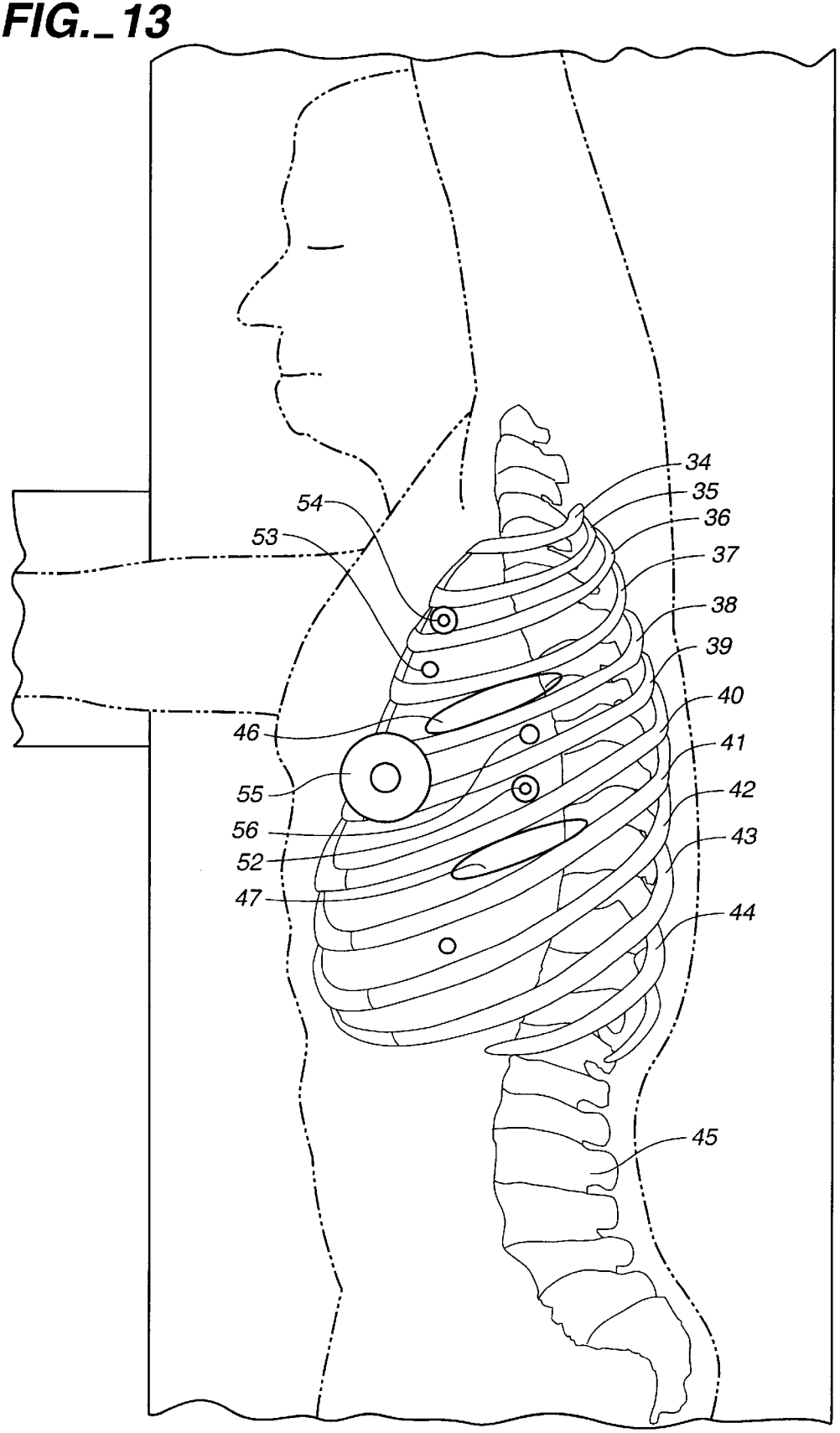

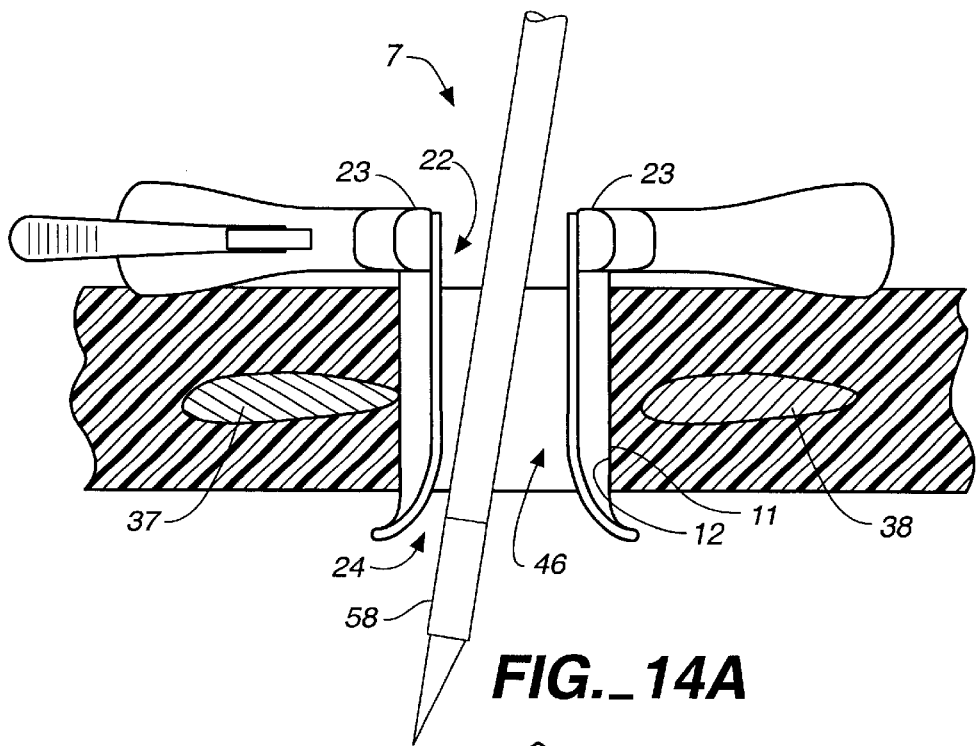
FIG._14A
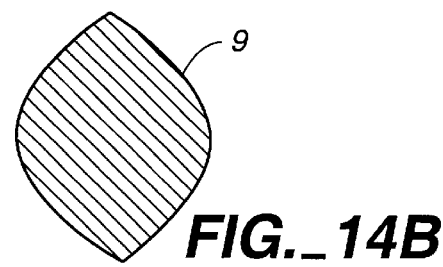
FIG._14B
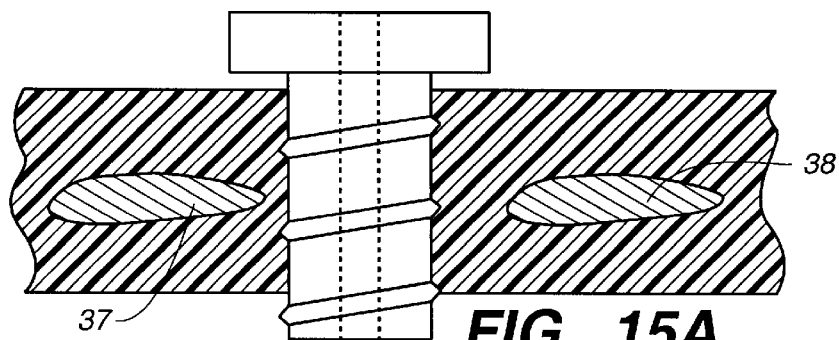
FIG._15A
(PRIOR ART)
FIG._15B

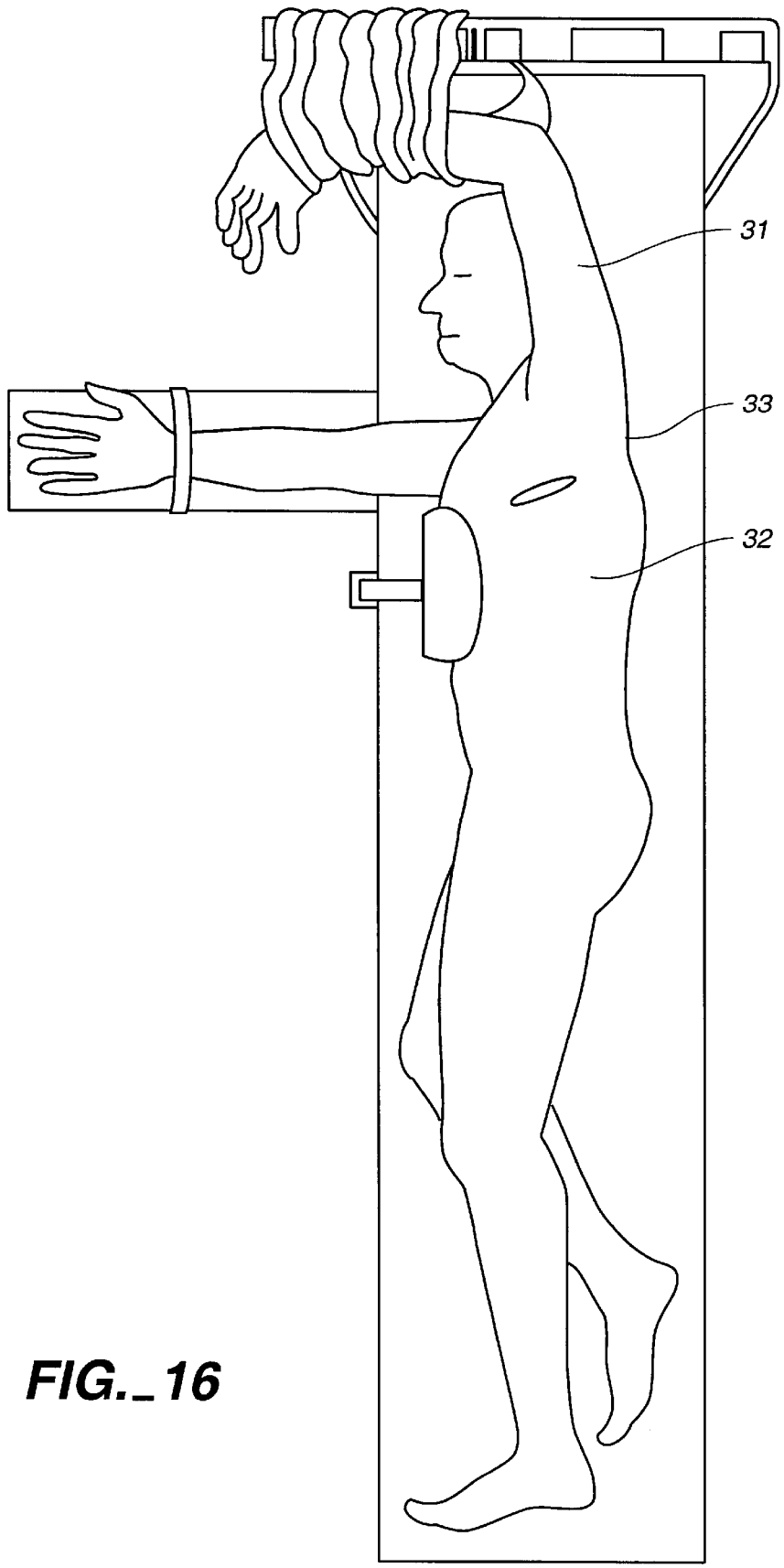
FIG._16

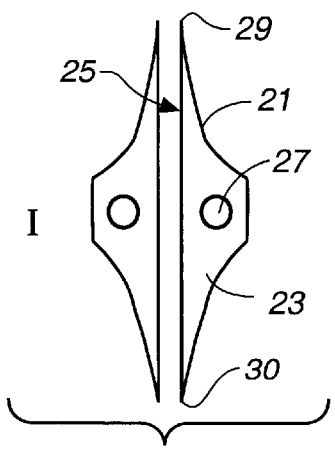
FIG._17A
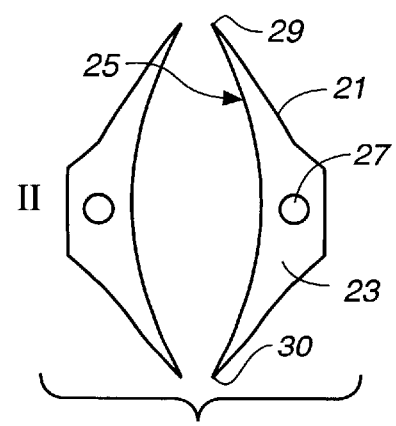
FIG._17B
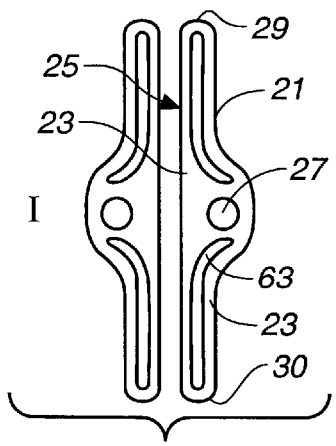
FIG._17C
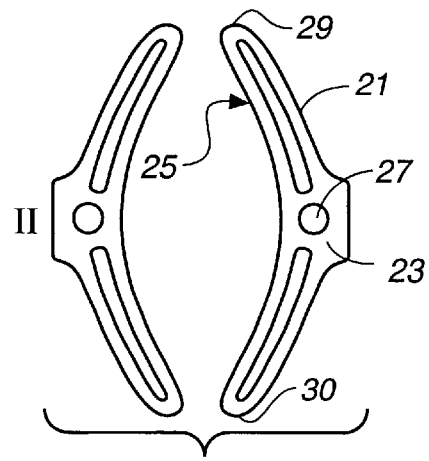
FIG._17D
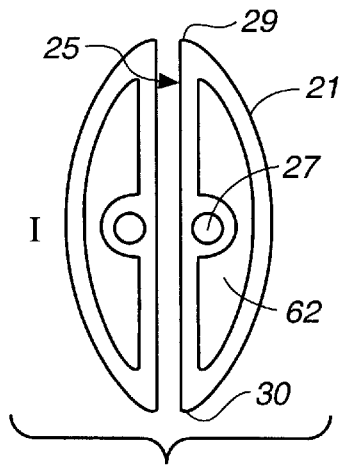
FIG._17E
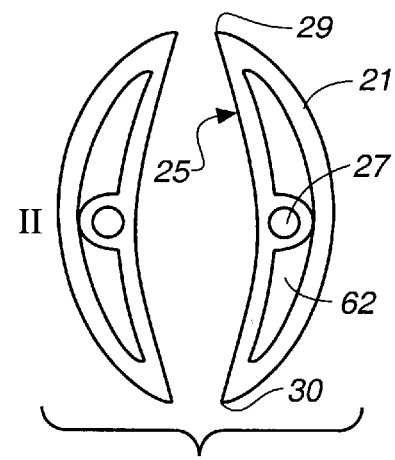
FIG._17F

SURGICAL RETRACTOR AND STABILIZING DEVICE AND METHOD FOR USE

CROSS-REFERENCE TO RELATED APPLICATIONS

This is a continuation-in-part of provisional patent application U.S. No. 60/014,922 filed Apr. 10, 1996 in the name of inventors Arthur Bertolero, Raymond Bertolero and Jerome Riebman. This application is related to concurrently-filed patent applications ESTC-001/00WO, ESTC-001/03WO, ESTC001/04WO AND ESTC-001/05US. Each of the above-identified patent applications is incorporated herein by reference.

INTRODUCTION

1. Technical Field

This invention relates to an adjustable surgical retractor and its use for improving a surgeon's ability to perform closed-chest, video-assisted exploratory, diagnostic or surgical procedures on a patient. The invention also relates to unique blades useful in combination with the retractor.

2. Background

Surgery on the heart is one of the most commonly performed types of surgery that is done in hospitals across the U.S. Cardiac surgery can involve the correction of defects in the valves of the heart, defects to the veins or the arteries of the heart and defects such as aneurysms and thromboses that relate to the circulation of blood from the heart to the body. In the past, most cardiac surgery was performed as open-chest surgery, in which a primary median sternotomy was performed. That procedure involves vertical midline skin incision from just below the super sternal notch to a point one to three centimeters below the tip of the xiphoid. This is followed by scoring the sternum with a cautery, then dividing the sternum down the midline and spreading the sternal edges to expose the area of the heart in the thoracic cavity. This technique causes significant physical trauma to the patient and can require one week of hospital recovery time and up to eight weeks of convalescence. This can be very expensive in terms of hospital costs and disability, to say nothing of the pain to the patient.

Recently, attempts have been made to change such invasive surgery to minimize the trauma to the patient, to allow the patient to recover more rapidly and to minimize the cost involved in the process. New surgical techniques have been developed which are less invasive and traumatic than the standard open-chest surgery. This is generally referred to as minimally-invasive surgery. One of the key aspects of the minimally invasive techniques is the use of a trocar as an entry port for the surgical instruments. In general, minimally invasive surgery entails several steps: (1) at least one, and preferably at least two, intercostal incisions are made to provide an entry position for a trocar; (2) a trocar is inserted through the incision to provide an access channel to the region in which the surgery is to take place, e.g., the thoracic cavity; (3) a videoscope is provided through another access port to image the internal region (e.g., the heart) to be operated on; (4) an instrument is inserted through the trocar channel, and (5) the surgeon performs the indicated surgery using the instruments inserted through the access channel. Prior to steps (1)–(5), the patient may be prepared for surgery by placing him or her on a cardiopulmonary bypass (CPB) system and the appropriate anesthesia, then maintaining the CPB and anesthesia throughout the operation. See U.S. Pat. No. 5,452,733 to Sterman et al. issued Sep. 26, 1995 for a discussion of this technique.

While this procedure has the advantage of being less invasive or traumatic than performing a media, sternotomy, there are numerous disadvantages to using trocars to establish the entry ports for the instruments and viewscope. For example, the trocars are basically "screwed" into position through the intercostal incision. This traumatizes the local tissues and nerve cells surrounding the trocar.

Once in place, the trocar provides a narrow cylindrical channel having a relatively small circular cross-section. This minimizes the movement of the instrument relative to the longitudinal axis and requires specially-designed instruments for the surgeon to perform the desired operation (See, e.g., the Sterman patent U.S. Pat. No. 5,452,733). In addition, because of the limited movement, the surgeon often has to force the instrument into an angle that moves the trocar and further damages the surrounding tissue and nerves. The need to force the instrument causes the surgeon to lose sensitivity and tactile feedback, thus making the surgery more difficult. The surgical retractor of this invention is designed to reduce the initial trauma to the patient in providing access to the internal region, to reduce the trauma to the patient during surgery, to provide the surgeon with greater sensitivity and tactile feedback during surgery, and to allow the surgeon to use instruments of a more standard design in performing the non-invasive surgery.

Other less invasive surgical techniques include access to the region of the heart to be corrected by anterior mediastinotomy or a thoracotomy. In a mediastinotomy, an incision is made that is two to three inches in length of a parasternal nature on the left or the right of the patient's sternum according to the cardiac structure that needs the attention in the surgery. Either the third or the fourth costal cartilage is excised depending on the size of the heart. This provides a smaller area of surgical access to the heart that is generally less traumatic to the patient. A thoracotomy is generally begun with an incision in the fourth or fifth intercostal space, i.e. the space between ribs 4 and 5 or ribs 5 and 6. Once an incision is made, it is completed to lay open underlying area by spreading the ribs. A retractor is used to enlarge the space between the ribs.

At the present time, when either of these techniques are used, a retractor is used to keep the ribs and soft tissues apart and expose the area to be operated on to the surgeon who is then able to work in the surgical field to perform the operation. The types of retractors that are used may be seen, for example, in volume 1 of *Cardiac Surgery* by John W. Kirkland and Brian G. Barratt-Boyes, Second Edition, Chapter 2, at page 101. Commercial-type retractors for minimally-invasive surgery that are useful for a mediastinotomy or a thoracotomy are manufactured by Snowden Pencer (the ENDOCABG rib spreader and retractor), U.S. Surgical (the mini CABG system), and Cardiothoracic Systems (the CTS MIDCAB™ System). The ENDOCABG refractor is two opposing retractor arms that are interconnected by a ratchet arm having a thumbscrew which can adjust the distance between the retractor arms. While this provides a useful retractor, it has certain shortcomings in its ease of use. The mini CABG System is an oval-based platform to which a number of retractors are then fitted around the extremity of the universal ring base and adjusted by a gear tooth connection. Each of the retractors have to be separately adjusted and there are other devices that can be connected to the universal base which can aid the surgeon in damping the heart movement to better work on the artery or vessel to which the surgeon is directing his attention. The CTS MIDCAB™ System serves a similar function to the ENDOCABG retractor, but is more complex. The designation CABG refers to "coronary artery bypass graft."

Major disadvantages of these systems include their limited positioning, complexity, and lack of reusability. It has now been discovered that the shortcomings of the retractors that are known in the prior art can be overcome with a new design as set forth in the following description.

OBJECTS OF THE INVENTION

An object of this invention is to provide a surgical retractor that is useful in exploratory or diagnostic work on a patient or preparing for and/or performing cardiac and other types of surgeries.

Another object of this invention is to provide a surgical retractor that is easier to use than the surgical retractors presently available.

Another object of this invention is to provide a surgical retractor that defines a larger opening than a surgical trocar through which a surgeon can insert surgical, exploratory or diagnostic instruments.

Another object of this invention is to provide a surgical retractor that can be used for both anterior or lateral access to the thoracic cavity, access to the abdominal cavity or exposure of an subcutaneous body structure.

Another object this invention is to provide a surgical retractor having removable blades, thus providing the surgeon with the flexibility to choose a size and shape blade to fit a patient's anatomy.

A further object of the invention is to provide a retractor that is less traumatic to the patient on whom an operation is being performed. This may allow the patient to recover more rapidly and create less disability for the patient.

A further object of this invention is to provide a surgical retractor that is less complex than the retractors presently commercially available and that requires fewer steps to operate.

Still a further object of this invention to provide improved access to and dissection of the left interior mammary artery.

Still a further object of the invention to provide a retractor that allows the surgeon to perform minimally invasive surgery while providing the surgeon with a similar instrument sensitivity tactile feedback to the operation as an open chest surgery.

Still a further object of this invention to provide a surgical retractor providing access to the internal organs of a person wherein the surgeon has a smooth surface on which to stabilize his instruments during the operation.

Another object of this invention is to provide a surgical retractor that provides a surgeon with access to an internal cavity more quickly.

Other objects of the invention may be apparent to one of ordinary skill in the art upon further meeting the following specification and claims.

SUMMARY OF THE INVENTION

One aspect of this invention is an adjustable surgical retractor that comprises
  (a) two handles suitable for grasping positioned opposite each other and pivotally connected so that the handles move reciprocatingly relative to each other,
  (b) a head means connected to each handle so that each head means moves reciprocatingly relative to the other,
  (c) a means for locking the heads at a preset distance from each other,
  (d) each head means having a connector means suitable for connecting a blade, and
  (e) a blade connected to each head means through the connector means with each blade having a width, depth and thickness so that the width extends substantially parallel to the length of the head and the depth extends downward from the top of the head means. The blades when taken together at the position of closest proximity to each other are of a size suitable to be inserted into a surgical incision in a patient undergoing a surgical procedure then spread apart to form an elongated access opening through which a medical instrument may be inserted to perform exploratory, diagnostic or surgical procedures.

Another aspect of this invention is a blade suitable for use as part of a surgical retractor, which blade comprises a biocompatible material having dimensions defined by a width, depth and thickness, the width and the depth defining an first and an second face separated from each other by the thickness of the blade, wherein the blade has a connector means for attaching to a head means of the surgical retractor.

Another aspect of this invention is a method of providing surgical access to a patient, which method comprises making a surgical incision through the skin and soft tissue of the patient,
  inserting two blades of a surgical retractor perpendicularly through the incision, and
  spreading the blades of said retractor to provide a relatively symmetrical, elongated channel for internally accessing said patient, said channel being defined by said blades wherein the internal faces of the blades have a concave surface to define a substantially ovoid channel, each blade having a smooth, continuous upper surface.

Another aspect of this invention is a method of performing minimally invasive surgery on a patient, which method comprises
  making a surgical incision through the skin and soft tissue of the patient,
  inserting two blades of a surgical retractor, perpendicularly through the incision,
  spreading the blades of said retractor to provide a relatively symmetrical, elongated channel for internally accessing said patient, said channel being defined by said blades wherein the internal faces of the blades have a concave surface to define a substantially ovoid channel, each blade having a smooth continuous upper surface,
  inserting a surgical instrument through said substantially ovoid channel, and
  performing a surgical procedure using the surgical instrument so inserted.

BRIEF DESCRIPTION OF THE DRAWINGS

FIG. 1 is a top view of the surgical retractor of this invention in the closed position with the proximal ends of the retractor shown at the bottom of the page and the distal end at the top.

FIG. 1A is the side view taken along line 1A–1A' shown in FIG. 1.

FIG. 1B is an end view along line 1B–1B'.

FIG. 2 is a top view of the retractor of this invention with the blades spread open.

FIG. 3 is a top view of a retractor of this invention having finger holds on the proximal grasping end of the retractor, the retractor being in the closed position.

FIG. 3A is a top view of the retractor of FIG. 3 shown in the open position.

FIG. 4 is a side view along lines 4F–4F' of the retractor of FIG. 3.

FIG. 5 is a top view of the surgical retractor of this invention similar to FIG. 3 but with a shorter handle.

FIG. 6A is a top view of the retractor of this invention shown without the blades positioned on the head region of the handles and in the closed position.

FIG. 6B is a top view of the retractor of FIG. 6A in the spread open position.

FIG. 6C shows the head region of the retractor in FIG. 6A having removable blades attached to the head member on a post as the connector means.

FIG. 6D is a side view of FIG. 6C.

FIG. 6E shows the head members of the surgical retractor with swiveling blades on the head member in the closed position.

FIG. 6F shows the head members in of FIG. 6E in the open position.

FIG. 7A shows an alternative design for the retractor of this invention where the handle has a roughened surface for improved grasping.

FIG. 7B is a side view along line 7B–7B' and showing a textured surface on the outside face of the blade.

FIG. 7C is a cross-sectional end view along line 7C–7C' of the blades positioned together in the head member of the surgical retractor.

FIG. 7D is an end view along line 7D–7D' showing the conjunction of the blades of the surgical retractor.

FIG. 7E shows the surgical retractor of FIG. 7A with the blades spread in the open position and the handles pulled together.

FIG. 8A is a perspective view of a blade of this invention having a slight curvature with a concave inner surface and a resilient outer surface.

FIG. 8B shows the relative distance of the upper and lower lip at the top and bottom of the blade.

FIG. 9A shows a pair of disposable retractor blades suitable for use with the retractor of FIGS. 1 through 7.

FIG. 9B is an alternative design for a pair of disposable retractor blades.

FIG. 9C is another design of the disposable retractor blade useful in this invention.

FIG. 9D shows a pair of disposable retractor blades as shown in 9A as they would look if they were flexed and attached to the retractor head and spread in an open position pushing against a patient's ribs.

FIG. 9E shows the blades of FIG. 9B as they would appear if they would be spread apart and used to spread the ribs in accordance with the process of this invention.

FIG. 9F is another design for the disposable retractor blades for use in this invention.

FIGS. 9G–9I show the various positions blades that swivel on the posts of FIG. 6C or 6D could take.

FIG. 9J shows tapered blades viewed along lines 9J–9J' in FIG. 9C.

FIG. 10A shows a perspective view of a design of blades having a lip at the top and bottom of the blade curling toward the convex face.

FIG. 10B shows a profile view of the blades showing the lip.

FIG. 11 shows the positioning of an incision in the intercostal space as used in the process of this invention.

FIG. 12A shows two retractors in place and stabilized by interconnecting bar shown in FIGS. 12B and 12C.

FIG. 12B shows an appropriate interconnecting bar.

FIG. 12C shows a notched interconnecting bar for interconnecting two retractors and stabilizing them.

FIG. 13 shows entry incision ports suitable for use for with the retractor of this invention in comparison to other trocars which are generally used for minimally invasive surgery.

FIG. 14A shows the greater degree of freedom that a surgeon would have in using the retractor of this invention as compared to a trocar shown in FIG. 15.

FIG. 14B is a cross-section of the elongated access opening.

FIG. 15A shows a trocar inserted into a patient between the ribs.

FIG. 15B shows the small cross-section of 15A.

FIG. 16 shows a patient positioned for a lateral incision using a retractor of this invention.

FIGS. 17A–17F show various preferred embodiments of the surgical blades of this invention.

DETAILED DESCRIPTION AND PRESENTLY PREFERRED EMBODIMENTS

While the description of the surgical retractor of this invention will be discussed primarily in relation to cardiac surgery procedures, it should be understood that the surgical retractor of this invention will find use in not only cardiac surgery but also laparoscopic surgery in which a surgeon wishes to gain access to an internal cavity by cutting the skin and going through the body wall in order to keep the incision spread apart so that surgical instruments can be inserted.

Thus the surgical retractor can find use in providing surgical access generally where a limited incision is desired. It is useful for subcutaneous access as well as for surgically accessing various body cavities such as the abdominal region, the thoracic region and the extremities.

It should also be understood that the surgical retractor of this invention can be used for direct access to an internal organ for surgical purposes with direct viewing of the work that's going on but it is preferably used in conjunction with video assisted cardiac surgery. In such a case, the surgical retractor of this invention is used in combination with a video endoscope that is positioned through a similar surgical retractor, a trocar or a percutaneous access opening which allows the scope to be positioned such that the internal work on the area to be operated on is transmitted to a video screen and the surgeon then performs the operation by viewing the screen and judging the use of the instruments with the assistance of the video endoscope. The surgical retractor has particular value in minimally invasive surgical techniques used in cardiac surgery.

One aspect of this invention is an adjustable surgical retractor. The retractor comprises
- (a) two handles suitable for grasping positioned opposite each other and pivotally connected so that the handles move reciprocatingly relative to each other,
- (b) a head means connected to each handle so that each head means moves reciprocatingly relative to the other,
- (c) a means for locking the heads at a preset distance from each other,
- (d) each head means having a connector means suitable for connecting a blade, and
- (e) a blade connected to each head means through the connector means with each blade having a width, depth and thickness so that the width extends substantially parallel to the length of the head and the depth extending downward from the top of the head.

The blades, when taken together at the position of closest proximity to each other are of a size suitable to be inserted into a surgical incision in a patient undergoing a surgical procedure then spread apart to form an elongated, ovoid access opening through which a medical instrument may be inserted to perform exploratory, diagnostic or surgical procedures.

Preferably, the surgical retractor is designed so that each blade has an inside face and an outside face. The inside face of each blade faces the inside face of the other blade and the outside face of each blade is designed to (i) minimize the trauma to the patient's body at the incision when the head means and blades are spread apart, (ii) stabilize the blades in the incision and (iii) allow customization for each patient's anatomy.

Referring now to FIG. 1, one sees the adjustable surgical retractor of the invention generally designated as 2. The retractor is characterized by having a elongated handle 4R and 4L for the right and left side as shown in FIG. 1. The elongated handles have a grasping end shown as 6L and 6R for the left and right sides of the device which are proximal to the user. On the opposite end, distal from the grasping handle are the ends 8L and 8R, again indicating the left and the right side as shown in the figure. Generally, the ends 8L and 8R when in the closed position shown in FIG. 1 will be in contact and there will generally be a space between opposing jaws of the device 9L and 9R. The handles which are suitable for grasping and are positioned opposite to each other are pivotally connected at pivot point which will have a male member pivot pin 10 which will correspond to a female receiving member 11 to allow the pivoting to take place. Thus the opposite ends 8L and 8R that are distal to the grasping handles comprise heads that are connected to each elongated handle so that each head moves reciprocatingly relative to the other. When handles 6L and 6R are drawn together as shown in FIG. 2, the distal ends or heads 8L and 8R are spread apart. A key to the utility of this particular design is the presence of a locking means to lock the heads at a preset distance from each other. The means shown in this case is a ratchet segment 14 having teeth 16 along the arcuate member 15 interconnecting handles 4L and 4R. Working in concert with the ratchet segment 14 and its corresponding teeth 16 is a corresponding pawl member 18 which is pivotally mounted at pivot 19, not shown, working in concert so that the teeth 20 on pawl 18 (as shown in FIG. 2) are complementary to the teeth 16 and provide a means for locking the heads at a preset distance from each other. Because of the numerous teeth 16 along ratchet member 14 the distance between head members 8L and 8R can vary significantly and in small incremental amounts. When pawl member 18 is disengaged from the ratchet segment 14 by not having the teeth in contact, tensioning means 12 tends to keep the handles 6L and 6R apart. Thus if the teeth are not engaged, the handles will tend to be spread apart by the tensioning means so that the heads 8L and 8R are generally in contact and ready for insertion prior to a surgical operation.

Each head means (which is shown as being unitary with the handle) has a connector means suitable for connecting a connector blade 22 to the corresponding heads 8L and 8R of elongated handles 4L and 4R. A blade 22 is connected to the head member of the elongated handle 4 by a connector means not shown, with each blade 22 having a width, depth and thickness dimensions that define the blade. The width, for purposes of this invention, is said to extend substantially parallel to the length of the head or handle. The top of the blade as seen as 23 in FIG. 1 such that while in use, the blade would be inserted into the surgical incision and the top edge 23 would remain outside the patient's surgical opening. The depth of the blade would extend downward from the top 23 of the blade into the surgical incision. Thus by looking at the side view of FIG. 1A, the bottom of the blade 22 would be shown as 24. The thickness of the blade is shown in FIG. 1 by the approximate extension dotted line at the head of the retractor device. The bottom of blades 24, when taken together at the position of closest proximity to each other as shown in FIG. 1, are of a size suitable to be inserted into a surgical incision in a patient undergoing a surgical procedure. Once inserted, the blades are then spread apart as shown in FIG. 2 to form an elongated access opening through which a medical instrument may be inserted to perform exploratory or surgical procedures as discussed hereinafter. The view of FIG. 1A of the surgical retractor of this device is a side view along lines 1A to 1A' in FIG. 1A while an end view along lines 1B to 1B' is shown in FIG. 1B. The numbers in each of FIGS. 1, 1A, 1B and 2 all designate similar parts of the device.

Turning now to FIG. 3, one can see an alternative configuration for the surgical retractor of this invention. In FIG. 3, the same numerals that are used in FIG. 1 are used as well. The only difference here is that the grasping handle 6L and 6R has a slightly modified design that allows the surgeon using the retractor to insert a thumb and other digit to grasp the handle at 7L and 7R of the proximal end 6L and 6R. Otherwise the operation of the retractor is the same as that shown in FIG. 1 and FIG. 2. FIG. 4 is a side view of the surgical retractor along lines 4F and 4F' showing the inserted edge 24 of blade 22 of the retractor. FIG. 3A shows the surgical retractor in the open position where the blades are spread apart.

Referring again to FIGS. 1, 1A, 1B and 2, one can see certain preferred aspects of the invention. Each blade for the retractor has an inside face and an outside face. The outside face can be seen in FIGS. 1A and 1B. The outside face of the blade is designed to minimize the trauma to the patient's body at the incision when the head means and the blade are spread apart and to further stabilize the blade in the incision. To minimize the trauma and stabilize the blade, it is preferred that the outside surface of the blade be of a finish that is slightly irregular and preferably is of a texture that is less traumatizing than a smooth, hard texture. In general the blades are made of a material which is strong enough to withstand the pressure of opening the retractor in the manner in which it is to be used. For example, if an incision is made in between the fourth and fifth ribs in the intercostal area, the ribs will have to be spread apart and the blades will have to be strong enough to withstand the pressure of gently spreading apart the ribs. Thus material for the blades may be of any material which is biocompatible with the patient's body and using it in the incision. The materials that can be used are stainless steel, plastic such as polyvinyl chloride (PVC), polyethylene, polyesters of various sorts, polycarbonate, teflon coated metal and the like. In addition to, or as an alternative to, the irregular surface of the outside face of the blade, the outside face may be padded or resilient to a certain extent to minimize the trauma to the surrounding tissue as it is spread open. Thus the blade may be of a laminated construction which has a stronger material on the interface with the outerface having a spongier or padded characteristic.

Preferably, the surgical retractor blade will be designed so that the upper edge 22 of each blade when spread apart has a concavely smooth surface corresponding to a concave surface of the interface which will be suitable for resting a surgical instrument against. This allows for much better movement of the instruments, e.g. in dissection of an internal mammary artery (IMA) and suturing of vessels. This can be seen in FIGS. 1 and 2, particularly in FIG. 2 where the concave surface is shown as number 25 for each blade connected to head 8L and 8R. Preferably there will be a lip at both the top edge 23 and the bottom edge 24 as shown in FIG. 1B. A slightly rolled edge is important for maintaining the blade in place so that the heads are spread open as shown in FIG. 2. In some instances it is preferred that the blade is of a flexible material such as a plastic with the outer face having a slightly irregular surface to stabilize the blade in the incision. In that case, the blades, when inserted onto the heads of the retractor, can be essentially parallel to each other but as the blades are spread apart, the ends would tend to bend towards each other forming the concavity shown in FIG. 2.

Alternatively, the blades may be preformed so that they have a lip or ridge on both the top 23 and the bottom 24 and have a preformed concavity that forms as the two interfaces rest against each other. This can be seen at FIGS. 8A, 8B, 10A and 10B. In this manner where each blade is rigid and the inner face of each is concave relative to the other where the outwardly protruding lip or ridge 23 on the upper and lower edge 24 of each blade, the blades are maintained in the incision when the head and the blades are spread apart after insertion into the patient's surgical incision. Where a patient's abdominal region is being accessed the lower lip will have to extend more than if the thoracic region is being accessed through the rib cage. Generally the lip at the top edge 23 shown in FIG. 10B will extend out about ⅜" with the bottom lip 24 extending about ⅛" when entering intercostally. If abdominal access is desired the lower lip 24 will have to extend out further. The dimensions shown in FIG. 8B will vary with individual patients. However, a particularly useful size for X is about 1.5 inches, for Y is about ⅜ inch and for Z is about ⅛ inch. A preferable aspect to the surgical retractor of this invention is that the blades are removable. The surgeon can select a blade having the desired width and depth to create exactly the size opening he or she wants, depending on a patient's size, shape, age, anatomy, etc., and the type of operation to be performed, e.g. lifting the left IMA for dissection. This is a particularly attractive aspect of the invention because the handles and the rest of the mechanism can be made of a durable, sterilizable material such as stainless steel. The blades can be made of a material that is re-sterilizable, and may be reusable or disposable, thus making the device easier and cheaper for the surgeon to use the device. For example, at the present time the commercially available devices through U.S. Surgical and CTS are very expensive and can be used only once because they have numerous parts and they all cannot be resterilized. By having removable blades 22 that can be disposed of, the surgical retractor 2 can be used multiple times by simply sterilizing then adding new disposable blades.

Preferably, the connector means on the head member of the surgical retractor that is suitable for connecting the blade is simply a male pivot pin as shown in FIGS. 6A–6F. Here the pivot pin, which is at the distal end of the surgical retractor, is shown as 26L and 26R. The surgical retractor blade which is removable has a reciprocal female receiving port 27 into which the pivot pin will slip. The pivot pin may be designed to lock the blade in place or to allow the blade to rotate as shown in FIG. 6E–6F. When the surgical retractor's handles are extended outwardly as shown in FIG. 6A, the blades would be together as shown in FIG. 6E where the male pivot pin seated in the female receiving port 27 as shown. As the proximal ends 6L and 6R are pulled together through grasping means 7L and 7R, the blades are pulled apart and can swivel slightly to adjust to the tension in the process of spreading apart the ribs.

The blades which are useful in the surgical retractor of this device are of a width, depth and thickness which will allow the surgeon access to the internal organs of the patient once an incision is made. Generally, the width of each blade may vary between about 1 inch to about 4 inches preferably 1 inch to about 3 inches. The depth will be of a sufficient depth to be adequately retained within the surgical incision when the head of the retractor are spread apart. Generally this depth will be about 1 inch to about 3 inches depending on the size and weight of the patient. The thickness, of course, will be of sufficient thickness to withstand the pressures of spreading apart the ribs of the patient if that's how the retractor is to be used. The thickness will depend on the strength and flexibility of the material used in making the blade. Generally, the thickness will be about one-eighth inch to about three-quarters of an inch.

When the blades are flexible, it is preferable that the male pivot pin receiving means is designed to frictionally receive the blade and retain it without pivoting. If, however, the material is of a metallic nature such as stainless steel and is inflexible, then it's preferable that the pivot pin would allow the inflexible blade to pivot freely on the post. Thus if blades of the approximate dimensions mentioned above are used it can be seen that the surgical opening could have a length of about 1 inch to about 4 inches and a width of about one-quarter inch to about two inches.

Turning now to FIG. 7A–7E one sees a variation on the design of the retractor of this invention. Here, the same numbers designate the same parts as in the previous FIGS. 1 through 6F. The difference between the design in FIG. 1 and FIG. 7A is simply that the handles 4L and 4R have notches designated at 5L and 5R to provide a better grasp for the surgeon using the retractor. These can be seen in both FIGS. 7A and 7B, 7B being the side view along lines 7B and 7B'. In addition, the handles 6R and 6L may have an additional notch designated as 28 for receiving a stabilizing bar which the surgeon can use to connect two surgical retractors of this invention. This is discussed hereinafter in greater detail. The cross-sectional end view of the device along lines 7C, 7C' shows a cross-section of the blade having the top edge 23 slightly expanded and curved outwardly to form a lip at the top edge. At the bottom edge 24 similarly the blade is curved outwardly to form a smaller lip. By having these lips, the retractor when used will tend to stay in place to a greater extent than in the absence of the lips. By viewing FIG. 7D, which is an end-on view, along lines 7D, 7D', one can see the end view showing the outer side 21 of the blade 22 having a resilient material attached thereto to minimize the trauma and to maximize the friction to assist in maintaining the blade in place when in use. FIG. 7A shows the retractor with the heads closed while FIG. 7E shows the retractor with the head and the blades in an open position spread apart. Of course, the locking mechanism for maintaining the retractor in a spread, open position operates in the same manner as explained for FIGS. 1 through 6.

Turning now to FIG. 8A, one can see a close-up of a blade having the concave inner surface and convex outer surface along with a top lip 23 which is more exaggerated than the bottom lip 24. In general, the top lip might be anywhere from a quarter to a three-quarters of an inch, generally about three-sixteenths of an inch at the widest point with the bottom lip generally being somewhat less than that amount, about an eighth of an inch, to about a half an inch, generally about an eighth of an inch. These dimensions are further shown in FIG. 8B.

Turning now to FIGS. 9A through 9F, one can see a perspective view the designs of the pairs of blades that would be used in the retractor of this invention. These blades are designed to be disposable and may be made of any materials that would be appropriate for the construction shown. In FIG. 9A, one sees a set of blades that have a top edge 23 and a bottom edge 24 along with a distal edge 29 and a proximal edge 30. Here, both the distal and proximal edges are shown as being rounded. The inside face 25 of the two blades is shown to be essentially straight, although it can be designed to be slightly convex as shown in FIG. 9B, if desired. A blade when attached to the connector means of the head member of the surgical retractor and expanded against the ribs when the retractor is in use will generally provide a convex outer surface 21 and a concave inner surface when the blade is of a flexible material. This is thought to be due to the fact that the female receiving port 27 in the blade 22 would receive the male pivot pin which would be the strongest portion of the blade and which would provide the outward stress to spread the ribs. Thus, the central portion of the blade would tend to spread out further than the distal and proximal edges, 29 and 30 respectively.

In FIG. 9B, one can see that there is a taper from the central portion of blade 22 where the female receiving port 27 is found to the distal edge 29 as well as to the proximal edge 30. Here the blade is somewhat an elongate, ovoid in shape and would take a shape similar to that shown in 9E when used with the surgical retractor in the manner designed. Alternatively, the design shown in 9C in essence shows a crescent shape for each of the blades wherein the opposing faces of the internal sides 25 are essentially parallel while the outside face 21 of each blade is convex. When in use, this too would take the configuration generally shown in FIG. 9E. Still another configuration is shown in FIG. 9F. Here the inner faces 25 are essentially parallel to the outer faces 21 and the edges of the proximal and distal edges 30 and 29, are somewhat blunter than those shown in either FIGS. 9A, 9B or 9C. This blade would take a configuration shown in FIG. 9D. In each of the disposable blades shown in FIGS. 9A through 9F, when viewed along line 9J–9J' as shown in FIG. 9C, the lower edge 24 is slightly tapered to minimize the amount of space needed for the initial insertion of the blades as attached to the surgical device.

Particularly useful configurations of the disposable blades of this invention are shown in FIG. 17A–17C. In the figures the numbers used to designate the part are the same as in FIGS. 9A–9J. Here in FIG. 17A one sees a blade which is thicker in the midsection than at the ends somewhat similar to the configuration in 9B and 9C. The view here is a direct top down view showing distal end 29 and proximal end 30 along with the inside face 25 and outside face 21. The top side is shown as 23 and the female receiving means is shown as 27. When the blade is fitted on to the corresponding male fastening means or post and the blades of the surgical retractor are spread apart the blade to the left in FIG. 17A will take the configuration shown in configuration number 2 as compared to configuration number 1 which shows the blade at rest. The primary spreading force will be at the center of the blade 27 and an elongated oval shaped opening will be formed as a result of the spreading of the blades. Turning now to FIG. 17B one sees a slightly different design wherein an internal channel 62 which aids in the cushioning effect of the blade. Here when the blade is attached to the head means through the male pivot pin which fits into the female receptor 27 and the retractor is spread apart to spread apart tissue and ribs as earlier discussed the blade will flex as shown in II and the cutout channel will straighten as shown in the diagram in the right part of FIG. 17B. The channel 62 has a slightly curved part 63 that will straighten somewhat to form the silhouette shown in II at 17B. Thus the outer wall 21 prevents the blade from flexing too much when expanded and the channel 62 provides a cushioning effect so that the inner face 25 pushes against the outer wall 21 by compressing channel 62 while making a greater opening between the convex surfaces 25 of the blade. Alternatively in FIG. 17C one can see the channel extending from the proximal edge of the blade 29 to the distal edge of the blade 30. Here when the blade is attached to the male connector means which is inserted into the female receptor and the retractor and expanded then the design which has an essentially flat face 35 changes to that silhouette shown in II. Here the outer wall defined by 21 bears the force of the flexion of the blade and prevents the limbs of the blade from flexing too much. The air channel compresses to add some cushioning effect and flexibility against the tissues to reduce the trauma to the tissues.

In use, the surgical retractor of this invention can be employed either in the anterior or lateral position on the chest for thoracic retraction. Preferably, it is employed laterally and in surgery the patient would be positioned to expose the lateral side of the patient to the doctor. This position is shown in FIG. 16 where the arm 31 of the patient is raised to expose the lateral side 32 of the patient to the doctor. The back 33 is positioned as shown. In the semi-cutaway view of FIG. 11 one can see how the retractor of this invention would work. Here the patient would be positioned similar to that shown in FIG. 16 with the arm 31 raised to expose the lateral side of the patient. The ribs shown as numbers 34 through 44 are attached to the spine shown roughly as 45 with intercostal spaces between the ribs. Incisions 46 and 47 are shown as being made between ribs 4 and 5 and 7 and 8. Once the incision is made, the retractors are used in accordance with FIG. 12. Here, the retractors are shown inserted with the head spread open to provide access for the surgeon to enter the thoracic cavity. The retractors may be connected in accordance with the use of connecting rods shown in FIGS. 12B or 12C and connected in accordance with the use of a retractor having a notch in the handle similar to that shown in FIG. 7B. The connecting rod may be of a design shown in FIGS. 12B and 12C as configuration 48 or 50. Once the retractors 2U and 2L are in place, creating the elongated opening or windows, into the thoracic cavity, in intercostal spaces between the fourth and fifth ribs shown as 46 in between the 7th and 8th ribs shown as 47. The positioning for a bar such as that shown in 48 and 50 in FIGS. 12B and 12C respectively, may be accomplished by several ways. In one mechanism, a screw down mechanism is used, shown as 48a and 48b in FIG. 12C. By using the positioning bars with the retractors, the retractors are secured to enable the retractors to be angled at the appropriate angle toward the heart or other structure to enable a diagnostic or therapeutic procedure is to be carried out. The angles of retractors to 2U and 2L is such that a 5° to 50° angle of the instruments relative to a perpendicular line through the opening is achieved. This provides the surgeon with an angle of access and a range of movement that is similar to that of an open heart surgical procedure. Locking screws 49A and 49B are shown where the solid bar 48 is rigid. While the bar is shown as straight it may optionally be slightly curved to contour to the shape of the rib cage. In FIG. 12C, positioning bar 50 is made of interlocking metal pieces with an interior wire that when tightened locks the position of the shape of the bar into place and the securing screws shown as 51a and 51b are shown protruding from one side of the interlocking metal pieces.

FIG. 13 indicates the difference in the elongated opening or window approach and the port method reported by Sterman, et al. Elongated openings 46 and 47 show greater exposure and flexibility compared with the trocar port in performing the work. Using the trocars generally a port will be located at positions 52, 53, 54 and at 46. Alternatively, if a minimally invasive direct coronary artery bypass MID-CAB incision such as a sternotomy incision is used, it is done at 55. Whatever is used it is useful to provide a percutaneous opening 56 for a view scope and one or more additional instruments required for traction or manipulation of the thoracic cavity. It should be understood that the invention retractor can also be used for MIDCAB surgery where the entry is made anterially as compared to laterally.

Turning now to FIG. 14, one can see the greater degree of manipulation that a doctor would have using the surgical retractor of applicant's invention as compared to the trocar. With the surgical retractor one can see that one obtains a wider range of motion for a surgical instrument shown as 58. The view here is of the cross-section, end-on view that would be similar to that shown in FIG. 7E along lines 7C–7C' shown in FIG. 7a. Here you can see the top 23 of blade 22.

The bottom of the blade 24 sits inside the thoracic cavity. Ribs 4 and 5 are shown as 37 and 38. The flexibility of the opening 46 in such a case should be compared with the lack of flexibility in FIG. 15 where a trocar is used to enter the thoracic cavity. This is visualized better by viewing a top-down view of FIG. 14A that shows the cross-section of elongate opening 46 compared to the cross-section of opening 60 of trocar 59 in FIG. 15A.

Having described the details of the surgical retractor of this invention, one can now consider another aspect of the invention, namely a method of providing surgical access to a patient. The method comprises making a surgical incision through the skin and soft tissue of the patient, inserting two blades of a surgical retractor perpendicularly through the incision, and spreading the blades of said retractor to provide a relatively symmetrical, elongated channel for internally accessing said patient. The channel is defined by the blades wherein the internal faces of the blades have a concave surface to define a substantially ovoid channel, each blade having a smooth, continuous upper surface. The method of course, is best performed using the surgical retractor described hereinbefore.

The method is particularly valuable in cardiac surgery where the surgical incision is made intercostally for access to the patient's thoracic region. Generally, at least two surgical incisions are made intercostally and sufficiently spaced apart to allow for the insertion and spreading of the blades of two of said surgical retractors. Each pair of spread blades then provide a relatively symnmetrical, elongated channel for accessing the internal thoracic region of the patient. Preferably, two surgical incisions are made laterally on said patient, although the incisions may also be made anteriorly on said patient. As shown in FIG. 12A, the two surgical retractors may be interconnected by a stabilizing bar to fix their positions relative to the other. To provide viewing access to the patient's thoracic cavity a third incision is made to insert an image transmission means to transmit an image of the patient's internal thoracic region.

Another aspect of this invention is a method of performing minimally-invasive invasive surgery on a patient. The method comprises making a surgical incision through the skin and soft tissue of the patient, inserting two blades of a surgical retractor, perpendicularly through the incision, spreading the blades of said retractor to provide a relatively symmetrical, elongated channel for internally accessing said patient (the channel is defined by the blades wherein the internal faces of the blades have a concave surface to define a substantially ovoid channel, each blade having a smooth continuous upper surface), inserting a surgical instrument through said substantially ovoid channel, and performing a surgical procedure using the surgical instrument so inserted. The method preferably employs the retractor described herein. The size and shape of the retractor blades are chosen for the exact size opening desired. The smooth continuous upper surface allows the surgeon to carryout the surgical procedures more easily. This method is particularly suited for cardiac surgery when said patient is maintained on a cardiopulmonary by-pass machine and the surgical incision is made intercostally for access to the patient's thoracic region. Preferably at least two surgical incisions (preferably lateral) are made intercostally and sufficiently spaced apart to allow for the inserting and spreading of the blades of two of said surgical retractors, each pair of spread blades providing a relatively symmetrical, elongated channel for accessing the internal thoracic region of the patient.

What is claimed is:

1. An adjustable surgical retractor that comprises
   (a) two handles suitable for grasping positioned opposite each other and pivotally connected so that the handles move reciprocatingly relative to each other,
   (b) a head connected to each handle so that each head moves reciprocatingly relative to the other,
   (c) a means for locking the heads at a preset distance from each other,
   (d) each head having a post suitable for connecting a blade, and
   (e) a blade connected to each head through a receptacle to frictionally receive the post and swivel thereon, with each blade having a width, depth and thickness so that the width extends substantially parallel to the length of the head and the depth extends downward from the top of the head wherein the blades taken together at the position of closest proximity to each other are of a size suitable to be inserted into a surgical incision in a patient undergoing a surgical procedure then spread apart to form an elongated access opening through which a medical instrument may be inserted to perform exploratory or surgical procedures.

2. The surgical retractor of claim 1 wherein each blade has an inside face and an outside face, said inside face of each blade facing the inside face of the other blade and the outside face of each blade designed to (i) minimize the trauma to the patient's body at the incision when the head and blades are spread apart and (ii) stabilize the blades in the incision.

3. The surgical retractor of claim 1 wherein the upper edge of each blade when spread apart has a concavely smooth surface corresponding to a concave surface of the inner face and is designed to stabilize a surgical instrument when such instrument contacts it.

4. The surgical retractor of claim 3 wherein each blade comprises a flexible material with the outer face having a textured surface to stabilize the blade in the incision.

5. The surgical retractor of claim 4 wherein when the inner faces of the blades are in closest proximity, the length of each blade is parallel to the other.

6. The surgical retractor of claim 3 wherein each blade is a flexible material and the outer surface comprises a resilient material.

7. The surgical retractor of claim 1 wherein each blade is rigid and each inner face is concave relative to the other with an outwardly protruding lip on the upper and lower edge of each blade to assist in maintaining the blades in the incision when the head and blades are spread apart after insertion into the patient's surgical incision.

8. The surgical retractor of claim 1 wherein the blades are disposable.

9. The surgical retractor of claim 1 wherein the width of each blade is about one inch to about four inches, the depth is about one inch to about three inches and the thickness is about one-eighth inch to about three-quarters of an inch.

10. The surgical retractor of claim 1 wherein when the head and blades are spread apart a surgical opening having a length of about one inch to about four inches and a width of about one-quarter inch to about two inches.

11. A method of providing surgical access to the internal thoracic region of a patient, which method comprises making an intercostal, surgical incision through the skin and soft tissue of the patient, wherein the incision is sufficiently sized to allow for the insertion of a surgical retractor in the incision;

inserting two blades of a surgical retractor perpendicularly through the incision; and spreading the blades of said retractor to provide a relatively symmetrical, elongated channel for accessing the internal thoracic region of the patient, said channel being defined by said blades wherein the internal faces of the blades have a concave surface to define a substantially ovoid channel, each blade having a smooth, continuous upper surface.

12. The method of claim 11, wherein each said retractor comprises (a) two handles suitable for grasping positioned opposite each other and pivotally connected so that the handles move reciprocatingly relative to each other;

(b) a head connected to each handle so that each head moves reciprocatingly relative to the other;

(c) a means for locking each head at a preset distance from the other;

(d) each head having a connector means suitable for connecting a blade, and (e) a blade connected to each head through the connector means with each blade having a width, depth and thickness so that the width extends substantially parallel to the length of the head and the depth extending downward from the top of the head.

13. The method of claim 11, wherein at least two surgical incisions are made intercostally and sufficiently spaced apart to allow for the insertion and spreading of the blades of two of said surgical retractors, each pair of spread blades providing a relatively symmetrical, elongated channel for accessing the internal thoracic region of the patient.

14. The method of claim 11, wherein said two surgical incisions are made laterally on said patient.

15. The method of claim 11, wherein said two surgical incisions are made anteriorly on said patient.

16. The method of claim 11, wherein said two surgical retractors are interconnected by a stabilizing bar to fix their positions relative to the other.

17. The method of claim 11, wherein a third incision is made to provide access to the patient's thoracic cavity sufficient to insert an image transmission means to transmit an image of the patient's internal thoracic region.

18. A method of performing minimally-invasive cardiac surgery on a patient, which method comprises making an intercostal surgical incision through the skin and soft tissue of the patient, wherein the incision is sufficiently sized to allow for the inserting and spreading of the blades of a surgical retractor, inserting two blades of a surgical retractor, perpendicularly through the incision, spreading the blades of said retractor to provide a relatively symmetrical, elongated channel for accessing the internal thoracic region of said patient, said channel being defined by said blades wherein the internal faces of the blades have a concave surface to define a substantially ovoid channel, each blade having a smooth continuous upper surface, inserting a surgical instrument through said substantially ovoid channel, and performing a surgical procedure using the surgical instrument so inserted.

19. The method of claim 18, wherein said retractor comprises (a) two handles suitable for grasping positioned opposite each other and pivotally connected so that the handles move reciprocatingly relative to each other, (b) a head connected to each handle so that each head means moves reciprocatingly relative to the other, (c) a means for locking each head at a preset distance from the other, (d) each head having a connector means suitable for connecting a blade, and (e) a blade connected to each head through the connector means with each blade having a width, depth and thickness so that the width extends substantially parallel to the length of the head and the depth extending downward from the top of the head.

20. The method of claim 18, wherein said surgery is cardiac surgery and said patient is maintained on a cardiopulmonary by-pass machine.

21. The method of claim 20, wherein at least two surgical incisions are made intercostally and sufficiently spaced apart to allow for the inserting and spreading of the blades of two of said surgical retractors, each pair of spread blades providing a relatively symmetrical, elongated channel for accessing the internal thoracic region of the patient.

22. The method of claim 18, wherein said two surgical incisions are made laterally on said patient.

23. The method of claim 18, wherein said two surgical incisions are made anteriorly on said patient.

24. The method of claim 18, wherein said two surgical retractors are interconnected by a stabilizing bar to fix their positions relative to the other.

25. The method of claim 18, wherein a third incision is made to provide access to the patient's thoracic cavity sufficient to insert an image transmission means to transmit an image of the patient's internal thoracic region.

26. The method of claim 25, wherein the surgery is performed by the surgeon by manipulating the instruments viewing the image surgery so transmitted by the transmission means.

* * * * *